(12) United States Patent
Chen et al.

(10) Patent No.: US 12,616,963 B2
(45) Date of Patent: May 5, 2026

(54) CHROME-FREE COPPER CATALYSTS FOR FATTY ESTER HYDROGENOLYSIS/HYDROGENATION

(71) Applicant: BASF CORPORATION, Florham Park, NJ (US)

(72) Inventors: Jian-Ping Chen, Beachwood, OH (US); Arunabha Kundu, Beachwood, OH (US); Joseph C. Dellamorte, Beachwood, OH (US)

(73) Assignee: BASF CORPORATION, Florham Park, NJ (US)

( * ) Notice: Subject to any disclaimer, the term of this patent is extended or adjusted under 35 U.S.C. 154(b) by 638 days.

(21) Appl. No.: 18/013,613

(22) PCT Filed: Jun. 24, 2021

(86) PCT No.: PCT/US2021/038934
§ 371 (c)(1),
(2) Date: Dec. 29, 2022

(87) PCT Pub. No.: WO2022/005872
PCT Pub. Date: Jan. 6, 2022

(65) Prior Publication Data
US 2023/0249160 A1     Aug. 10, 2023

Related U.S. Application Data

(60) Provisional application No. 63/045,967, filed on Jun. 30, 2020.

(51) Int. Cl.
B01J 23/889     (2006.01)
B01J 21/04     (2006.01)
(Continued)

(52) U.S. Cl.
CPC ........... *B01J 23/8892* (2013.01); *B01J 21/04* (2013.01); *B01J 23/005* (2013.01); *B01J 23/34* (2013.01);
(Continued)

(58) Field of Classification Search
CPC ...... B01J 23/8892; B01J 35/45; B01J 35/613; B01J 35/77; B01J 35/612; B01J 35/40;
(Continued)

(56) References Cited

U.S. PATENT DOCUMENTS

| | | |
|---|---|---|
| 5,403,962 A | 4/1995 | Schneider et al. |
| 6,455,464 B1 | 9/2002 | Chen |

(Continued)

FOREIGN PATENT DOCUMENTS

| | | |
|---|---|---|
| EP | 3243566 A1 | 11/2017 |
| JP | H08-108072 A | 4/1996 |

(Continued)

OTHER PUBLICATIONS

Extended European Search Report issued Jul. 2, 2024 in European Patent Application No. 21834219.4, 8 pages.
(Continued)

*Primary Examiner* — James A Fiorito
(74) *Attorney, Agent, or Firm* — Peter DiMauro

(57)     ABSTRACT

A method of preparing a calcined hydrogenolysis/hydrogenation catalyst includes mixing a copper-containing material, manganese-containing material, sodium aluminate, and water to obtain an aqueous slurry; contacting the aqueous slurry with a caustic material to form a precipitate in a caustic aqueous slurry; removing the precipitate from the caustic aqueous slurry; and removing residual water from the precipitate to form a dried precipitate; calcining the dried precipitate to form the calcined hydrogenolysis/hydrogenation catalyst exhibiting a Brunauer-Emmett-Teller ("BET")
(Continued)

surface area of about 5 m$^2$/g to about 75 m$^2$/g. The calcined hydrogenolysis/hydrogenation catalyst may include a spinel structure crystallite size of about 15 nm or less. The calcined hydrogenolysis/hydrogenation catalyst may include a tenorite crystallite size of about 20 nm to 30 nm.

8 Claims, 26 Drawing Sheets

(51) Int. Cl.

| | |
|---|---|
| *B01J 23/00* | (2006.01) |
| *B01J 23/34* | (2006.01) |
| *B01J 23/72* | (2006.01) |
| *B01J 35/40* | (2024.01) |
| *B01J 35/45* | (2024.01) |
| *B01J 35/61* | (2024.01) |
| *B01J 35/77* | (2024.01) |
| *B01J 37/00* | (2006.01) |
| *B01J 37/02* | (2006.01) |
| *B01J 37/03* | (2006.01) |
| *B01J 37/04* | (2006.01) |
| *B01J 37/08* | (2006.01) |
| *B01J 37/18* | (2006.01) |
| *C07C 29/149* | (2006.01) |

(52) U.S. Cl.
CPC ............... *B01J 23/72* (2013.01); *B01J 35/40* (2024.01); *B01J 35/45* (2024.01); *B01J 35/612* (2024.01); *B01J 35/613* (2024.01); *B01J 35/77* (2024.01); *B01J 37/009* (2013.01); *B01J 37/0236* (2013.01); *B01J 37/031* (2013.01); *B01J 37/04* (2013.01); *B01J 37/088* (2013.01); *B01J 37/18* (2013.01); *C07C 29/149* (2013.01); *B01J 2235/15* (2024.01)

(58) Field of Classification Search
CPC . B01J 21/04; B01J 23/005; B01J 23/34; B01J 23/72; B01J 37/009; B01J 37/0236; B01J 37/031; B01J 37/04; B01J 37/088; B01J 37/18; C07C 29/149
See application file for complete search history.

(56) References Cited

U.S. PATENT DOCUMENTS

| | | |
|---|---|---|
| 2003/0069457 A1 | 4/2003 | Chen |
| 2017/0252727 A1 | 9/2017 | Paulus et al. |
| 2018/0065108 A1 | 3/2018 | Thakur et al. |
| 2019/0321808 A1 | 10/2019 | Pfanzelt et al. |

FOREIGN PATENT DOCUMENTS

| | | |
|---|---|---|
| JP | 2017-528313 A | 9/2017 |
| WO | 2014048957 A1 | 4/2014 |

OTHER PUBLICATIONS

International Search Report and Written Opinion for PCT/US2021/038934 mailed Oct. 19, 2021, 8 pages.

Example 8

Position °2θ

FIG. 21

CHROME-FREE COPPER CATALYSTS FOR FATTY ESTER HYDROGENOLYSIS/HYDROGENATION

CROSS-REFERENCE TO RELATED APPLICATION(S)

This application is a national stage entry under 35 U.S.C. § 371 of International Application No. PCT/US2021/038934, filed on Jun. 24, 2021, which claims the priority to U.S. Provisional Patent Application No. 63/045,967, filed on Jun. 30, 2020. The contents of these applications are hereby incorporated by reference herein in their entirety.

TECHNOLOGY

The present technology relates generally to the field of catalysts for hydrogenolysis/hydrogenation. More specifically, it is related to copper-manganese-aluminum based catalysts in powder form slurry phase for fatty acid ester hydrogenolysis/hydrogenation.

BACKGROUND

Commercial slurry processes for producing fatty alcohols typically employ copper-chromium (CuCr) catalysts. As environmental regulation becomes stricter on chromium containing chemicals or catalysts, it is crucial to develop catalysts that do not contain chromium but instead utilize other materials as both chemical and mechanical stability promoters.

SUMMARY

In one aspect, the present technology provides a method of preparing a calcined hydrogenolysis/hydrogenation catalyst, the method includes: mixing a copper-containing material, a manganese-containing solution, and sodium aluminate solution; adding a caustic material to form an aqueous slurry that includes a precipitate; collecting the precipitate; drying the precipitate to form a dried precipitate; and calcining the dried precipitate to form the calcined hydrogenolysis/hydrogenation catalyst; wherein: the calcined hydrogenolysis/hydrogenation catalyst exhibits a Brunauer-Emmett-Teller ("BET") surface area of about 5 $m^2/g$ to about 75 $m^2/g$; and the calcined hydrogenolysis/hydrogenation catalyst is substantially free of chromium. In some embodiments, the calcined hydrogenolysis/hydrogenation catalyst may have a spinel structure crystallite size of about 15 nm or less. In some embodiments, the calcined hydrogenolysis/hydrogenation catalyst may have a tenorite crystallite size of about 20 nm to 30 nm.

In another aspect, the present technology provides a calcined hydrogenolysis/hydrogenation catalyst prepared according to the method described herein in any embodiment.

In a related aspect, the present technology provides a hydrogenolysis/hydrogenation catalyst that includes: copper oxide; manganese oxide; and alumina; wherein the hydrogenolysis/hydrogenation catalyst has a Brunauer-Emmett-Teller ("BET") surface area of about 5 to about 75 $m^2/g$, and wherein the hydrogenolysis/hydrogenation catalyst is substantially free of chromium.

In another related aspect, the present technology provides a method of hydrogenating a carbonyl-containing organic compound, the method includes contacting the carbonyl-containing organic compound with a hydrogenolysis/hydrogenation catalyst that includes: copper oxide; manganese oxide; and alumina; wherein: the hydrogenolysis/hydrogenation catalyst exhibits a Brunauer-Emmett-Teller ("BET") surface area of about 5 to about 75 $m^2/g$.

BRIEF DESCRIPTION OF THE DRAWINGS

FIG. 21 is a graph comparing fatty alcohol yield as a percentage as a function of time and comparing example 8 to a standard CuCr catalyst, according to the examples.

DETAILED DESCRIPTION

Figure 1:
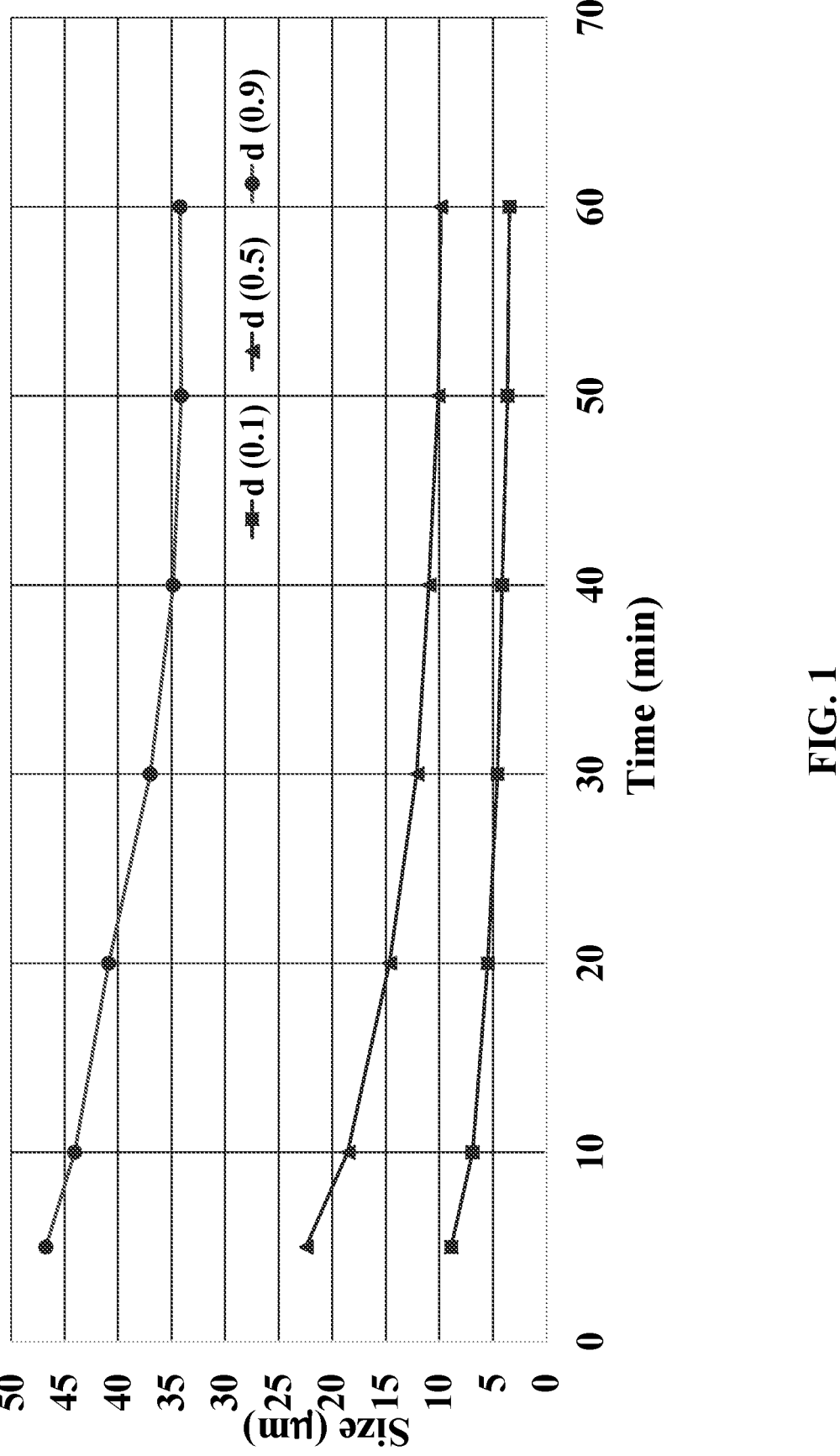
FIG. 1 is a three line graph showing particle size formation during precipitation by the size of $d_{10}$ (d=0.1), $d_{50}$ (d=0.5), and $d_{90}$ (d=0.9) for Example 1.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s).

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

The use of the terms "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

Described herein are copper-aluminum (Cu—Al) catalysts having manganese added as a promoter, and which are chromium-free. The addition of the manganese enhances the catalytic performance of the catalyst in terms of activity and selectivity. Surprisingly, the Cu—Mn—Al catalysts have been shown to exhibit higher activity and improved selectivity compared to commercially available CuCr catalysts. Generally, chromium-free catalysts have suffered from low mechanical stability during reaction conditions. However, here it has been surprisingly found that the manganese provides improved mechanical strength under reaction conditions, and good filtration properties. Filtration is important to fatty alcohol production when using slurry phase processes as the catalysts must be separated from the reactor slurry for reuse, and to allow for pure fatty alcohol products.

Accordingly, in one aspect, a method of preparing a calcined hydrogenolysis/hydrogenation catalyst is provided. As used herein, the term "hydrogenolysis/hydrogenation" refers to a catalyst, which in a particular application may catalyze either or both of a hydrogenolysis reaction or a hydrogenation reaction. The method includes mixing a copper-containing material, a manganese-containing solution, sodium aluminate solution, and water to obtain a solution mixture. The mixture is then contacted with a caustic material to form an aqueous slurry that includes a precipitate, where the precipitate forms upon contacting the mixture with the caustic material. The precipitate is then removed/collected from the aqueous slurry, and the material is dried to form a dried precipitate. Finally, the dried precipitate is calcined to form the calcined hydrogenolysis/hydrogenation catalyst. In any embodiment disclosed herein, the aqueous slurry may have a pH of about 6.0 to about 9.0. In any embodiment disclosed herein, the precipitate may be removed/collected via filtration.

As used herein, calcining refers to heating the precipitate in an oven under an air or controlled oxygen atmosphere. In various embodiments, the calcining is conducted at a temperature from about 400° C. to about 1200° C. This may include from about 600° C. to about 900° C., from about 500° C. to about 1000° C., or from about 600° C. to about 800° C. The calcining may be done for a time period to complete calcination of the dried precipitate. According to various embodiments, the time period may be for about 10 minutes to about 10 hours. This includes from about 0.5 hour to about 3 hours.

The drying of the precipitate may be done in an oven in a heated atmosphere. The heating may be from about 40° C. to about 200° C., from about 75° C. to about 150° C., or from about 100° C. to about 125° C. The drying may be done for a time period to ensure a dried precipitate. According to various embodiments, the time period may be from 1 hour to 24 hours, or more. This includes about 5 hours to about 15 hours, or about 8 hours to about 12 hours. In some embodiments, the drying is overnight.

The calcined hydrogenolysis/hydrogenation catalyst that is formed as a powder. It is not extruded or in the presence of a binder. As such, it exhibits a Brunauer-Emmett-Teller ("BET") surface area of about 5 m$^2$/g to about 75 m$^2$/g. This includes a BET surface area of about 20 m$^2$/g to about 70 m$^2$/g, or about 15 m$^2$/g to about 50 m$^2$/g. Related to surface area is the physical size of the particles of the powder. The sizes may be expressed in terms of d$_{10}$, d$_{50}$, and d$_{90}$. In one, illustrative, example, the d$_{50}$ for the calcined hydrogenolysis/hydrogenation is about 4 μm to about 12 μm.

The calcined hydrogenolysis/hydrogenation catalyst is substantially free of chromium. As used herein, substantially free is intended to indicate that chromium is excluded to the extent possible, but trace amounts of chromium may be carried due to contamination by chromium of the other starting reagents such as the copper, manganese, and aluminum source materials. However, where appropriate, substantially free of chromium means that the catalyst contains no detectable chromium (0.0 wt % chromium).

With regard to the materials/solutions that form the catalyst, they may include salts of copper and manganese. Illustrative copper salts include, but are not limited to, copper nitrate, copper sulfate, copper chloride, copper bromide, copper carbonate, copper acetate, or a mixture of two or more thereof. Illustrative manganese salts include, but are not limited to, manganese nitrate, manganese sulfate, manganese chloride, manganese bromide, manganese acetate, or a mixture of two or more thereof. According to some embodiments, the calcined hydrogenolysis/hydrogenation catalyst includes CuO from about 35 wt % to about 65 wt %, $Mn_2O_3$ from about 8 wt % to about 60 wt %, and $Al_2O_3$ from about 2 wt % to about 40 wt %.

With regard to the caustic material, illustrative materials include, but are not limited to, $Na_2CO_3$, NaOH, $K_2CO_3$, KOH, or a mixture of any two or more thereof.

It has also been observed that the calcined hydrogenolysis/hydrogenation catalyst exhibits various crystalline phases. It may exhibit a crystal phase that is CuO and one or more of $CuAl_2O_4$ and various spinel phases, $Cu_{1.5}Mn_{1.5}O_4$, $Cu_3Mn_3O_8$, $Cu_{0.451}Mn_{0.594}O_2$, or $MnAl_2O_4$. Without being bound by theory, it is believed that the presence of the spinel phase contributes to the higher performance and physical stability of the calcined hydrogenolysis/hydrogenation catalyst. $Cu^{2+}$ or $Mn^{2+}$ oxidation states are stable with spinel structures under reduction conditions, which minimize metal leaching under reaction media. In some embodiments, the calcined hydrogenolysis/hydrogenation catalyst exhibits a crystal phase of CuO with one or more of $CuAl_2O_4$, $Cu_{1.5}Mn_{1.5}O_4$, $Cu_3Mn_3O_8$, $Cu_{0.451}Mn_{0.594}O_2$, $Mn_2O_3$, or $MnAl_2O_4$, and the BET surface area of the calcined hydrogenolysis/hydrogenation catalyst is about 20 m²/g to about 70 m²/g.

In some embodiments, the calcined hydrogenolysis/hydrogenation catalyst may exhibit a crystal phase that may include from about 55 wt % to about 70 wt % of CuO in spinel structure. For example, the catalyst may include CuO in a spinel structure from about 55 wt. % to about 70 wt %, about 60 wt % to about 70 wt %, about 63 wt % to about 68 wt %, or any range including and/or in between any two of the preceding values. In some embodiments, the calcined hydrogenolysis/hydrogenation catalyst may exhibit a crystal phase that may include from about 30 wt % to about 45 wt % of CuO in tenorite structure. For example, the catalyst may include CuO in a tenorite structure from about 30 wt % to about 45 wt %, about 30 wt % to about 40 wt %, about 30 wt % to about 35 wt %, or any range including and/or in between any two of the preceding values. In some embodiments, the calcined hydrogenolysis/hydrogenation catalyst may have a spinel structure crystallite size of about 15 nm or less. Suitable spinal structure crystallite sizes may include, but is not limited to, about 1 nm to about 15 nm, about 5 nm to about 15 nm, about 10 nm to about 15 nm, about 10 nm to about 12 nm, about 12 nm to about 15 nm, or any range including and/or in between any two of the preceding values. In some embodiments, the calcined hydrogenolysis/hydrogenation catalyst may have a tenorite crystallite size of about 20 nm to about 30 nm. Suitable spinal structure crystallite sizes may include, but is not limited to, about 20 nm, about 21 nm, about 22 nm, about 23 nm, about 24 nm, about 25 nm, about 26 nm, about 27 nm, about 28 nm, about 29 nm, about 30 nm, or any range including and/or in between any two of the preceding values.

According to some embodiments, the method may further include reducing the calcined hydrogenolysis/hydrogenation catalyst in a hydrogen atmosphere to obtain a pre-reduced calcined hydrogenolysis/hydrogenation catalyst. In some embodiments, the reducing may be carried out in the presence of a solvent for a time, and at a temperature, sufficient to reduce the calcined hydrogenolysis/hydrogenation catalyst.

In another aspect, the calcined hydrogenolysis/hydrogenation catalyst prepared according to any of the methods described herein is provided.

In a further aspect, a method of hydrogenating a carbonyl-containing organic compound is provided. The method includes contacting the carbonyl-containing organic compound with any of the above calcined hydrogenolysis/hydrogenation catalysts. In various embodiments, the carbonyl-containing organic compound may include a ketone, an aldehyde, and/or an ester. In some embodiments, it is a fatty acid ester. More specifically, in any embodiment disclosed herein, the carbonyl-containing organic compound may include, but is not limited to, a fatty acid methyl ester (e.g. $C_8$-$C_{20}$ carbon chain), fatty acid wax ester (e.g. $C_{18}$-$C_{40}$ carbon chain), furfural, methyl phenyl ketone, di-methyl or di-ethyl esters, or a mixture of any two or more thereof.

The present invention, thus generally described, will be understood more readily by reference to the following examples, which are provided by way of illustration and are not intended to be limiting of the present invention.

EXAMPLES

Comparative Example. See Example 1 of U.S. Pat. No. 6,455,464. A $Cu(NO_3)_2$ solution (15.48 wt % Cu; 1640 g) is diluted in deionized water (2500 mL). A sodium aluminate (25 wt % $Al_2O_3$; 815.6 g) is diluted in deionized water (2500 mL). $Na_2CO_3$ (318 g) is dissolved in deionized water (1500 mL). In a 12-L tank, water (2500 mL) is added followed by simultaneous addition of the copper nitrate and sodium aluminate solutions at a rate of about 33 mL per minute. The $Na_2CO_3$ solution is then added to form a precipitate and to maintain the pH at about 7.4, by adjusting the rate of addition of the $Na_2CO_3$ solution at room temperature. After completion, the slurry that is formed of the precipitate is filtered to provide a filter cake. The filter cake is washed with deionized water (3000 mL) three or more times. The washed cake is then dried over night at 120° C. The resulting material is then calcined in air 700° C. for 2 hours to form a Cu—Al-oxide material. This material is used as a reference against other example materials.

Examples 1-6. A $Mn(NO_3)_2$ solution (45 wt % Mn; 200.3 g) is added to a $Cu(NO_3)_2$ solution (17 wt % Cu; 984.6 g), and the combined solution is diluted to 1 L with deionized water. A $Na_2Al_2O_4$ solution (45 wt %; 439 g) is diluted to 667 mL with deionized water. $Na_2CO_3$ (267 g) was dissolved in deionized water (1.33 L). Deionized water (1.33 L) was then added to a baffled strike tank with agitation (400 rpm), and the combined Cu/Mn solution was then added at a rate of 16 mL/min simultaneously with the Al solution at 11 mL/min. The $Na_2CO_3$ solution is then added to form a precipitate and to maintain the pH at about 7.0, by adjusting the rate of addition of the $Na_2CO_3$ solution at room temperature. After completion, the slurry that is formed of the precipitate is filtered to provide a filter cake. The filter cake is washed with deionized water (3000 mL) three or more times. The washed cake is then dried over night at 120° C. This preparation has a chemical composition of CuO (58 wt %)-$Mn_2O_3$ (12 wt %)-$Al_2O_3$ (30 wt %). With changing the final catalyst ratio of Cu/Mn and Cu/Al ratio and changing in metal solution addition sequence, a series of catalysts with different ratio of Cu/Mn/Al were prepared and tested.

Example 1 is without calcination, while Examples 2-6 are with calcination of the material at different temperatures of 650° C., 680° C., 700° C., 750° C., and 800° C., respectively.

Figure 2:
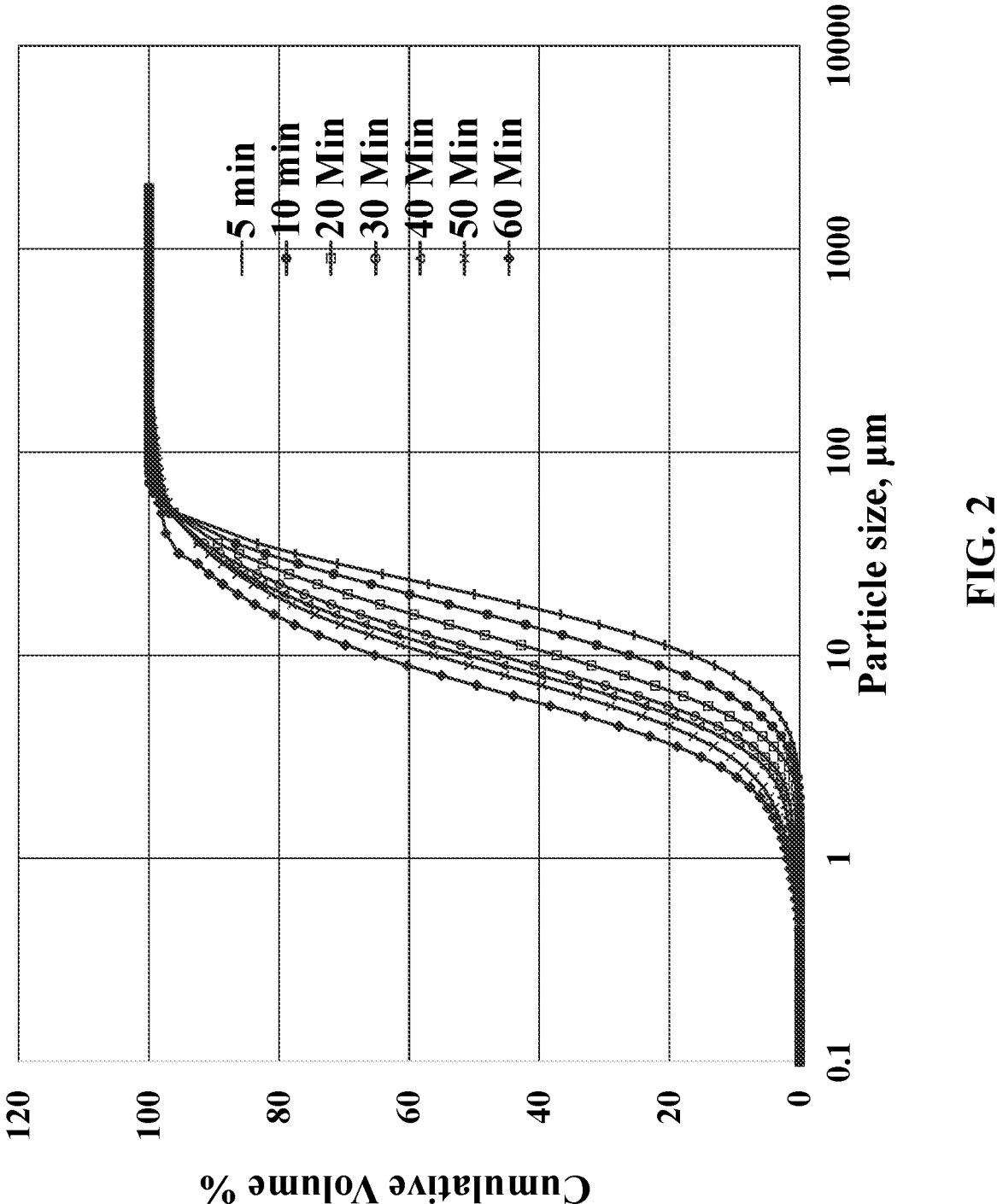
FIG. 2 is a graph relating to particle size formation as a function of time based upon "Volume In," according to Example 1. As described herein, each plot shows the Cumulative Volume % (vol %) distribution of particles detected via laser diffraction within a particle size range.
Figure 3:
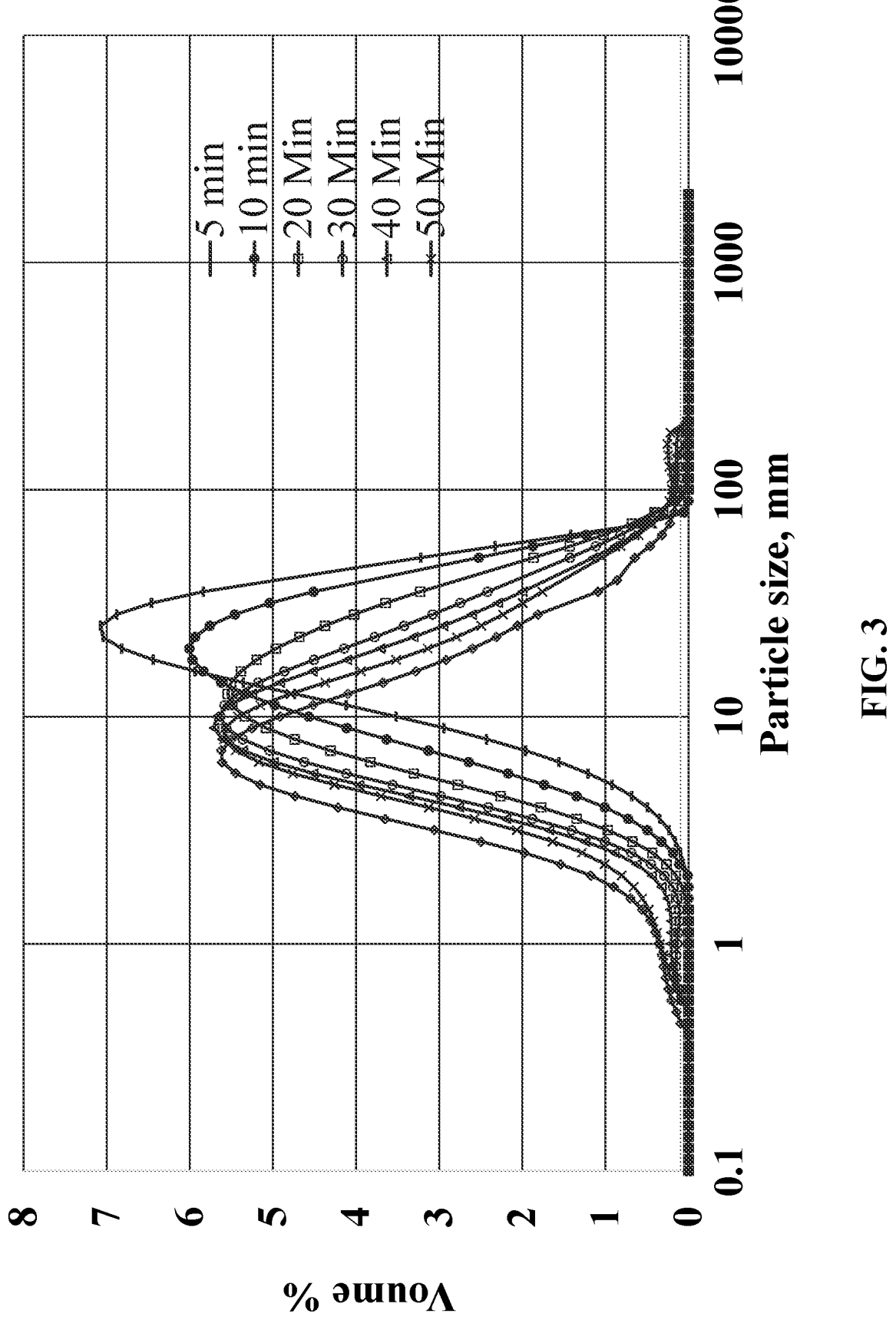
FIG. 3 is a graph relating to particle size formation as a function of time based upon "percent passing," according to Example 1. As described herein, each plot shows a normal distribution curve in which a majority of the sample volume is occupied by the mid-range sized particles (i.e., Volume %).

FIGS. 1-3 illustrate the particle size formation during precipitation in Example 1. In FIG. 1, the size is according to the $d_{10}$ (d=0.1), $d_{50}$ (d=0.5), and $d_{90}$ (d=0.9) values. FIGS. 2 and 3 provide volume particle distribution curves. FIG. 2 shows the Cumulative Volume % distribution of particles detected via laser diffraction at a particle size range. FIG. 3 shows a normal distribution curve in which a majority of the sample volume is occupied by the mid-range sized particles (i.e., Volume %). From this preparation, the catalyst has a particle size distribution of $d_{10}$ (3.4 μm), $d_{50}$ (9.9 μm), and $d_{90}$ (34.2 μm). The average particle size distribution $d_{50}$ is from about 7-12 μm.

Example 7. A $Mn(NO_3)_2$ solution (50 wt % Mn; 95 g), a $Cu(NO_3)_2$ solution (17.2 wt % Cu; 109 g), and $Al(NO_3)_3$ $9H_2O$ (13.3 g) are combined in a beaker and diluted with deionized water to a total of 1 L to form Solution A. Separately, a solution of $Na_2CO_3$ (23 wt %, 550 g) is prepared and forms Solution B. Solution B is slowly added to Solution A resulting in the precipitation of a Cu—Mn—Al hydroxyl carbonate slurry with a final pH of about 9. After completion, the slurry is filtered to provide a filter cake. The filter cake is washed with deionized water three or more times. The washed cake is then dried over night at 120° C. The dry powder is then calcined at 750° C. for 3 hours. This preparation has a chemical composition of CuO (40 wt %)-$Mn_2O_3$ (57 wt %)-$Al_2O_3$ (3 wt %).

Example 8. A $Mn(NO_3)_2$ solution (50 wt % Mn; 102 g), a $Cu(NO_3)_2$ solution (17.2% Cu; 109 g), and $Al(NO_3)_3$ $9H_2O$ (36 g) are combined in a beaker and diluted with deionized water to a total of 1 L to form Solution A. Separately, a solution of $Na_2CO_3$ (23 wt %, 230 g) is prepared and forms Solution B. Solution B is slowly added to Solution A resulting in the precipitation of a Cu—Mn—Al hydroxyl carbonate slurry with a final pH of about 6. After completion, the slurry is filtered to provide a filter cake. The filter cake is washed with deionized water three or more times. The washed cake is then dried over night at 120° C. The dry powder is then calcined at 750° C. for 3 hours. This preparation has a chemical composition of CuO (37 wt %)-$Mn_2O_3$ (55 wt %)-$Al_2O_3$ (8 wt %).

Analysis of Examples 1-8. As a summary of the comparative Example to Examples 2-8, Table 1 is a comparison of these examples.

TABLE 1

| Comparison of the Chemical Compositions. | | | |
|---|---|---|---|
| Example | CuO, wt % | $Mn_2O_3$, wt % | $Al_2O_3$, wt % |
| 1 (Comparative) | 61 | 0 | 39 |
| 2 | 58 | 12 | 30 |
| 3 | 58 | 12 | 30 |
| 4 | 58 | 12 | 30 |
| 5 | 58 | 12 | 30 |
| 6 | 58 | 12 | 30 |
| 7 | 40 | 57 | 3 |
| 8 | 37 | 55 | 8 |

BET (Brunauer-Emmett-Teller) surface area measurement is performed by following ASTM method D3663-03 Standard Test Method for Surface Area of Catalysts and Catalyst Carriers. A summary of the BET surface areas for the catalysts is provided in Table 2. As will be noted, higher calcination temperatures result in lower BET surface area. With BET surface areas from 5 to 70 $m^2/g$ all of the catalysts show good fatty alcohol yield from hydrogenolysis/hydrogenation of methyl esters.

TABLE 2

| BET Surface Areas. | | |
|---|---|---|
| Example | Calcination Temperature (° C.) | BET SA. ($m^2$/g) |
| 2 | 650 | 68.6 |
| 3 | 680 | 63 |
| 4 | 700 | 46.4 |
| 5 | 750 | 30.0 |
| 6 | 800 | 19.4 |
| 7 | 750 | 5.6 |
| 8 | 750 | 9.6 |

XRD (x-ray diffraction) analysis. XRD Analysis of Example 2 to 8 shows that the catalysts may be calcined from 500° C. to 950° C. to form CuO and one or more phases including $CuAl_2O_4$, $Cu_{1.5}Mn_{1.5}O_4$, $Cu_3Mn_3O_8$, $Cu_{0.451}Mn_{0.594}O_2$, and $MnAl_2O_4$ on the chemical compositions of the precipitates.

The XRD analysis was carried out using an Empyrean diffraction system with a copper anode tube using generator settings at 45 kV and 40 mA to produce Cu $K_{\alpha1}$ radiation of wavelength 1.54060 Å used to generate data. The optical path consisted of a 0.04 rad primary soller slit, 15 mm beam mask, 1° divergence slit, 2° anti-scatter slit, the sample, a monochromator, a secondary 0.02 rad soller slit, and an X'Celerator position sensitive detector. Each sample described below was ground to a fine powder using mortar and pestle and then backpacked into a round mount sample holder. The sample holder is loaded onto a sample spinner during data acquisition to improve particle counting statistics. The data collection from the round mount covered a range from 15° to 90° 2θ using a continuous scan with a step size of 0.017° 2θ and a time per step of 300 s. A graphite monochromator was used to strip unwanted radiation, including Cu $K_β$ radiation.

Panalystical HighScore version 4.5 software and ICDD PDF 4+ 2018 version 4.1801 powder diffraction file database was used for phase identification analysis. FIGS. 4-9 illustrate XRD pattern data for Examples 2-5, 7, and 8, respectively. As shown in the table below, the XRD pattern data shows peaks corresponding to the following phases for each respective catalyst.

TABLE 3

| XRD Crystal Phases | | |
|---|---|---|
| Sample ID | Sample Description | Phases |
| Example 2 | 650° C. | CuO; $CuAl_2O_4$ |
| Example 3 | 680° C. | CuO; $CuAl_2O_4$ |
| Example 4 | 700° C. | CuO; $CuAl_2O_4$; AlMn (trace) |
| Example 5 | 750° C. | CuO; $CuAl_2O_4$; $Cu_{1.5}Mn_{1.5}O_4$ |
| Example 7 | 750° C. | CuO; $Cu_{1.5}Mn_{1.5}O_4$; $Cu_3Mn_3O_8$ |
| Example 8 | 750° C. | CuO; $CuAl_2O_4$; $Cu_{1.5}Mn_{1.5}O_4$ |

Figure 4:
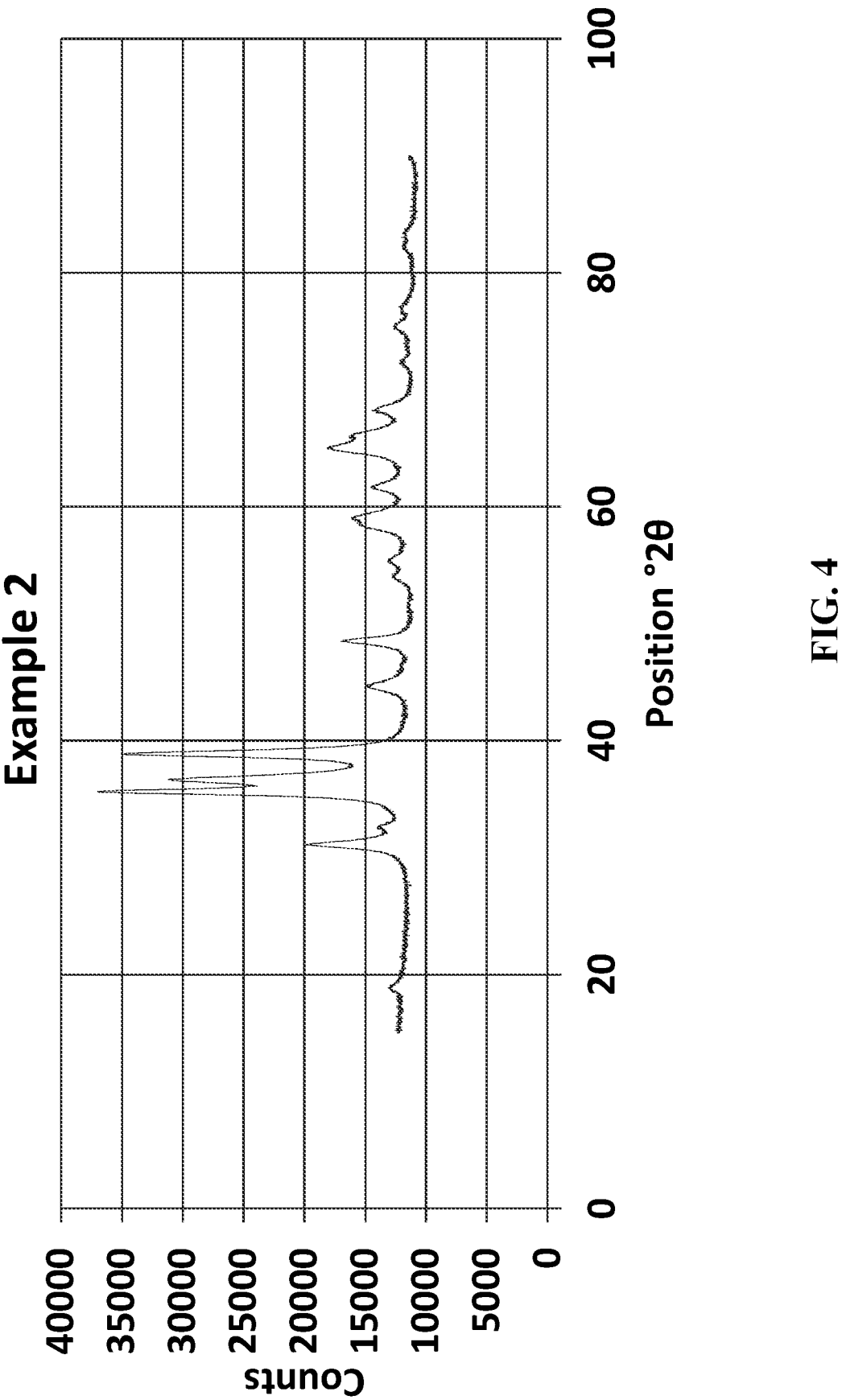
FIG. 4 is a graph showing the XRD spectra for the catalyst of Example 2, according to the examples.
Figure 5:
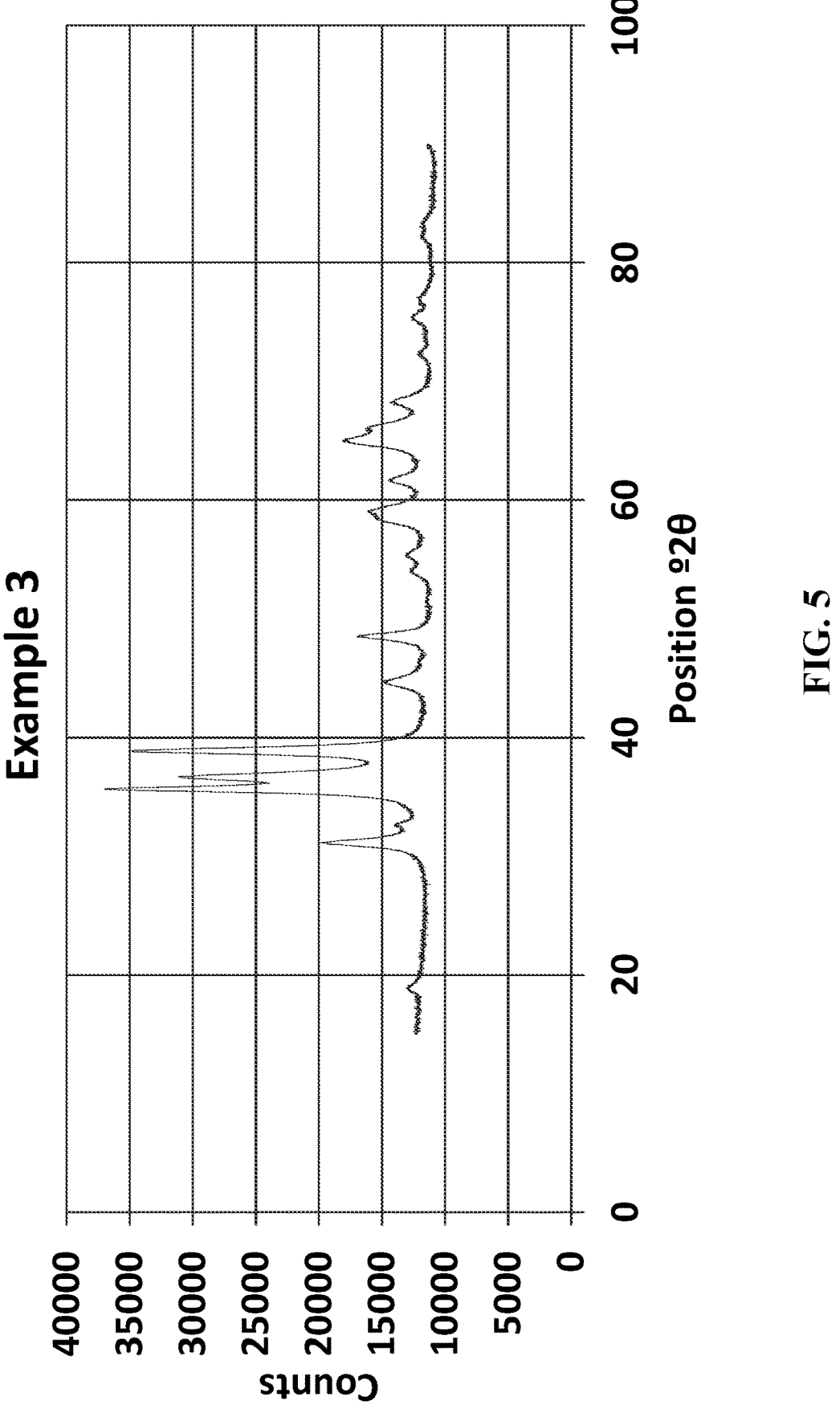
FIG. 5 is a graph showing the XRD spectra for the catalyst of Example 3, according to the examples.
Figure 22:
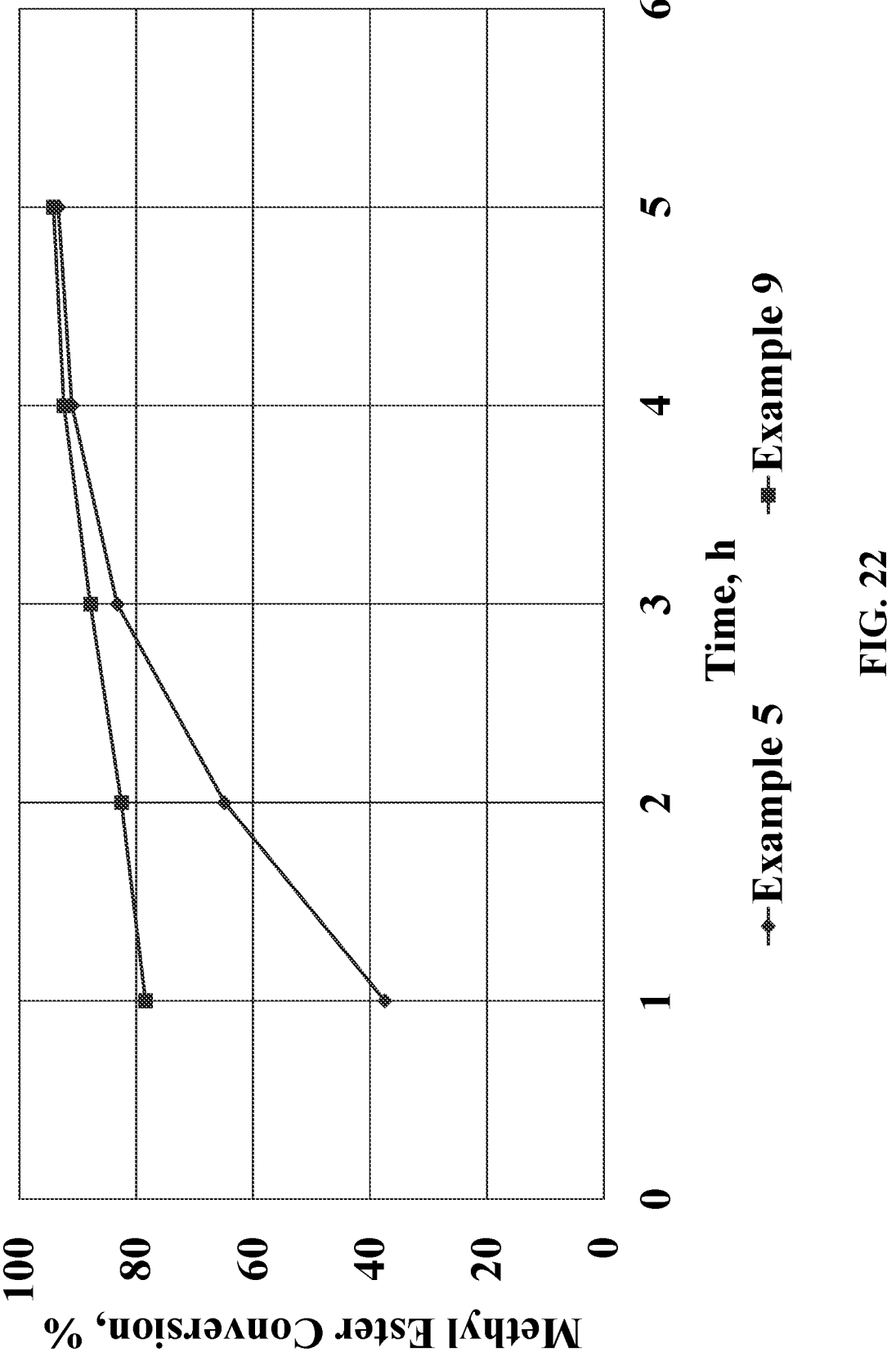
FIG. 22 is a graph comparing methyl ester conversion as a percentage as a function of time and comparing examples 5 and 9, according to the examples.

FIG. 4 shows representative XRD peaks for CuO and $CuAl_2O_4$ at 18.9, 31, 32.6, 35.5, 36.7, 38.9, 44.6, 46.4 48.9, 53.6, 55.5, 58.2, 58.9, 61.7, 64.8, 65.9, 67.9, 72.2, 75.3, 76.8, 82.1, and 83.2 for the Example 2 catalyst. FIG. 22 shows representative peaks for CuO and $CuAl_2O_4$ at 18.9, 31, 32.6, 35.5, 36.7, 38.9, 44.6, 46.4 48.9, 53.6, 55.5, 58.2, 58.9, 61.7, 64.8, 65.9, 67.9, 72.2, 75.3, 76.8, 82.1, and 83.2 for the Example 3 catalyst.

Figure 6:
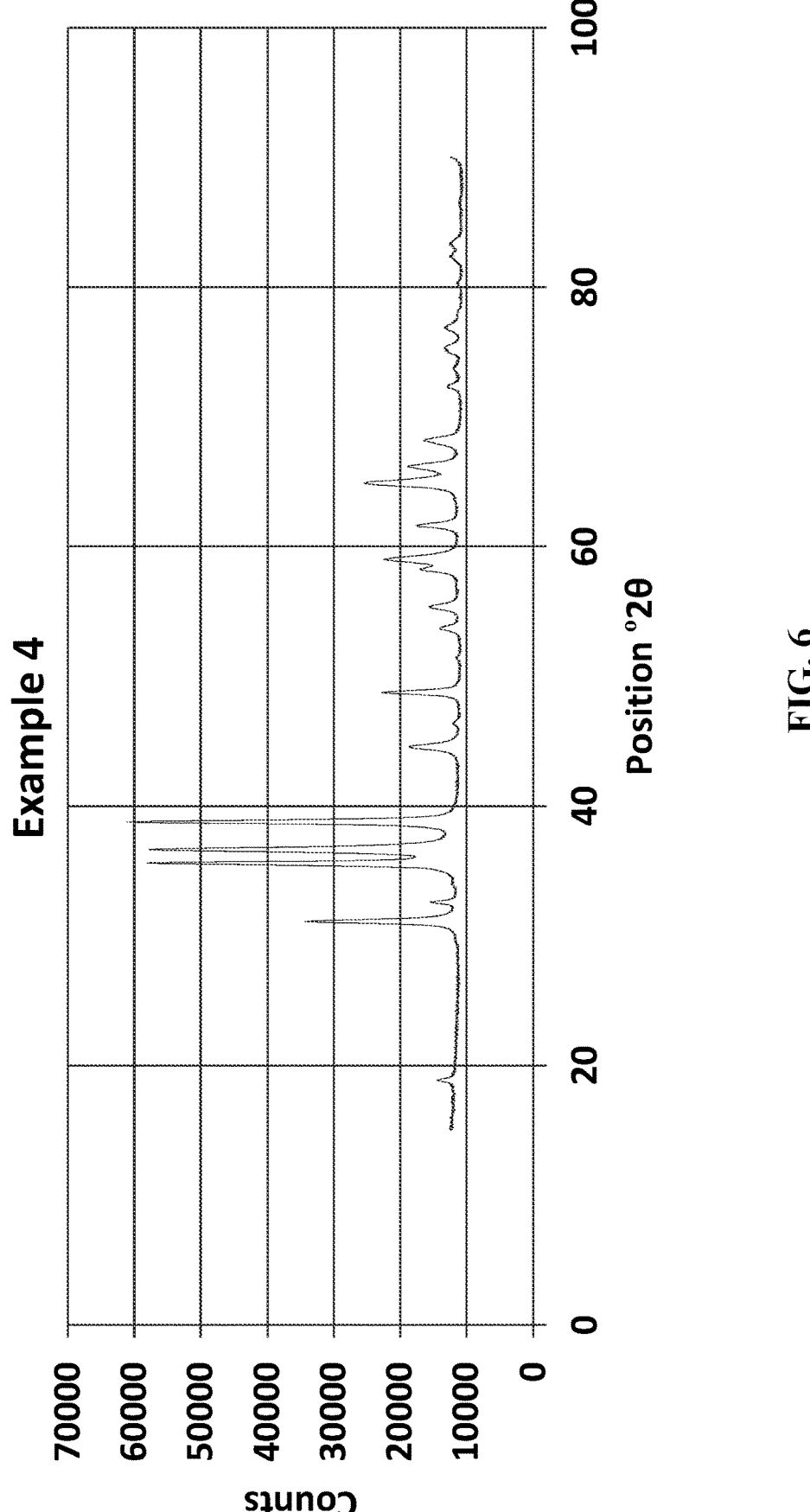
FIG. 6 is a graph showing the XRD spectra for the catalyst of Example 4, according to the examples.

FIG. 6 shows representative XRD peaks for CuO, $CuAl_2O_4$, and trace AlMn at 18.9, 31, 32.6, 34, 35.5, 36.7, 38.9, 44.6, 46.4 48.9, 51.2, 53.6, 55.5, 58.2, 58.9, 61.7, 64.8, 65.9, 67.9, 72.2, 75.3, 76.8, 82.1, and 83.2 for the Example 4 catalyst.

Figure 7:
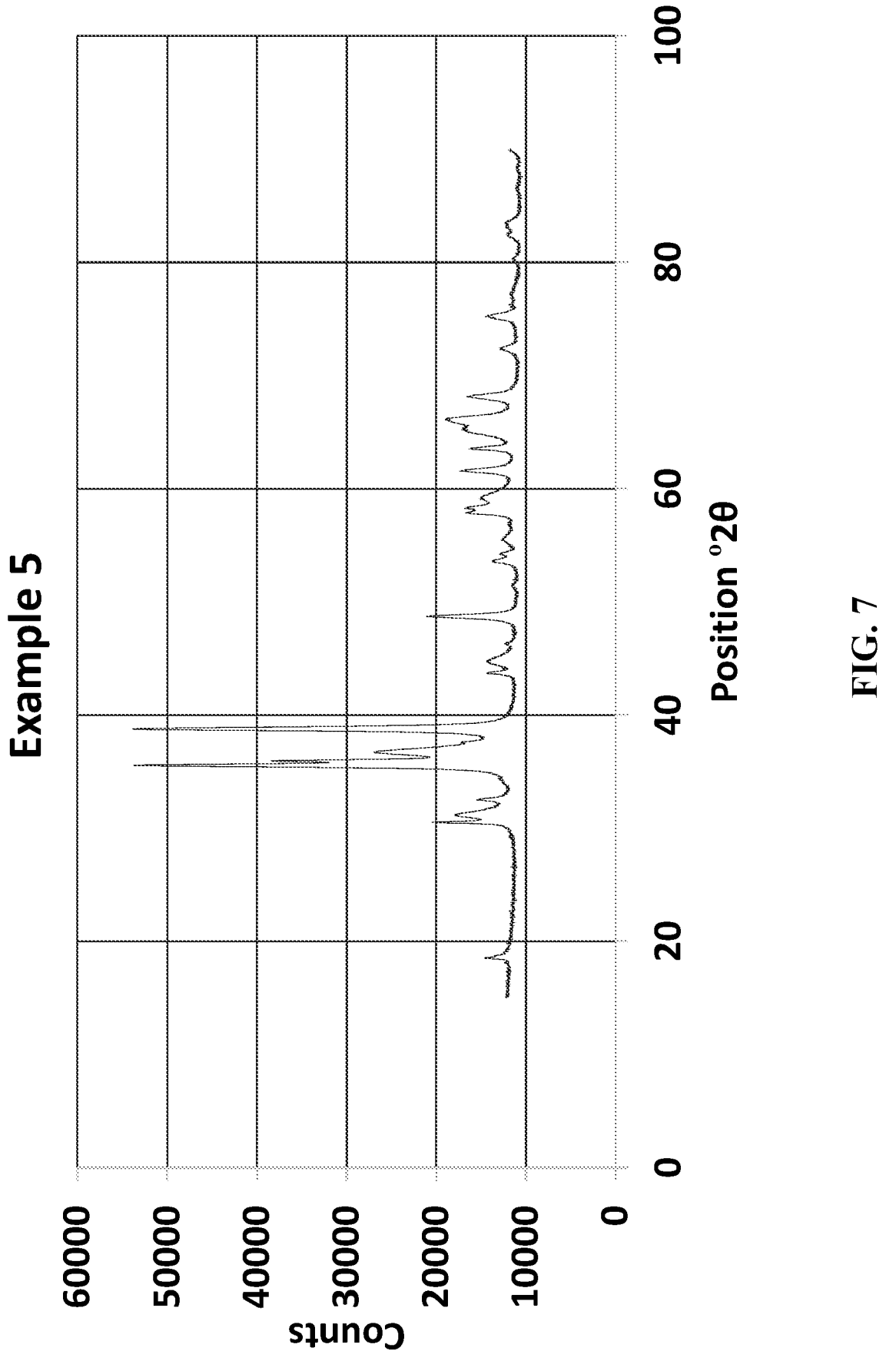
FIG. 7 is a graph showing the XRD spectra for the catalyst of Example 5, according to the examples.

FIG. 7 shows representative XRD peaks for CuO, $CuAl_2O_4$, and $Cu_{1.5}Mn_{1.5}O_4$ at 18.9, 30.5, 31.1, 32.6, 34.0, 35.5, 35.9, 36.7, 37.8, 38.9, 43.6, 44.6, 46.4 48.9, 51.2, 53.6, 54.2, 55.5, 57.9, 58.2, 59.3, 61.7, 63.5, 65.0, 65.9, 68.1, 72.2, 75.3, 76.1, 80.1, 82.1, 83.2, and 86.5 for the Example 5 catalyst.

Figure 8:
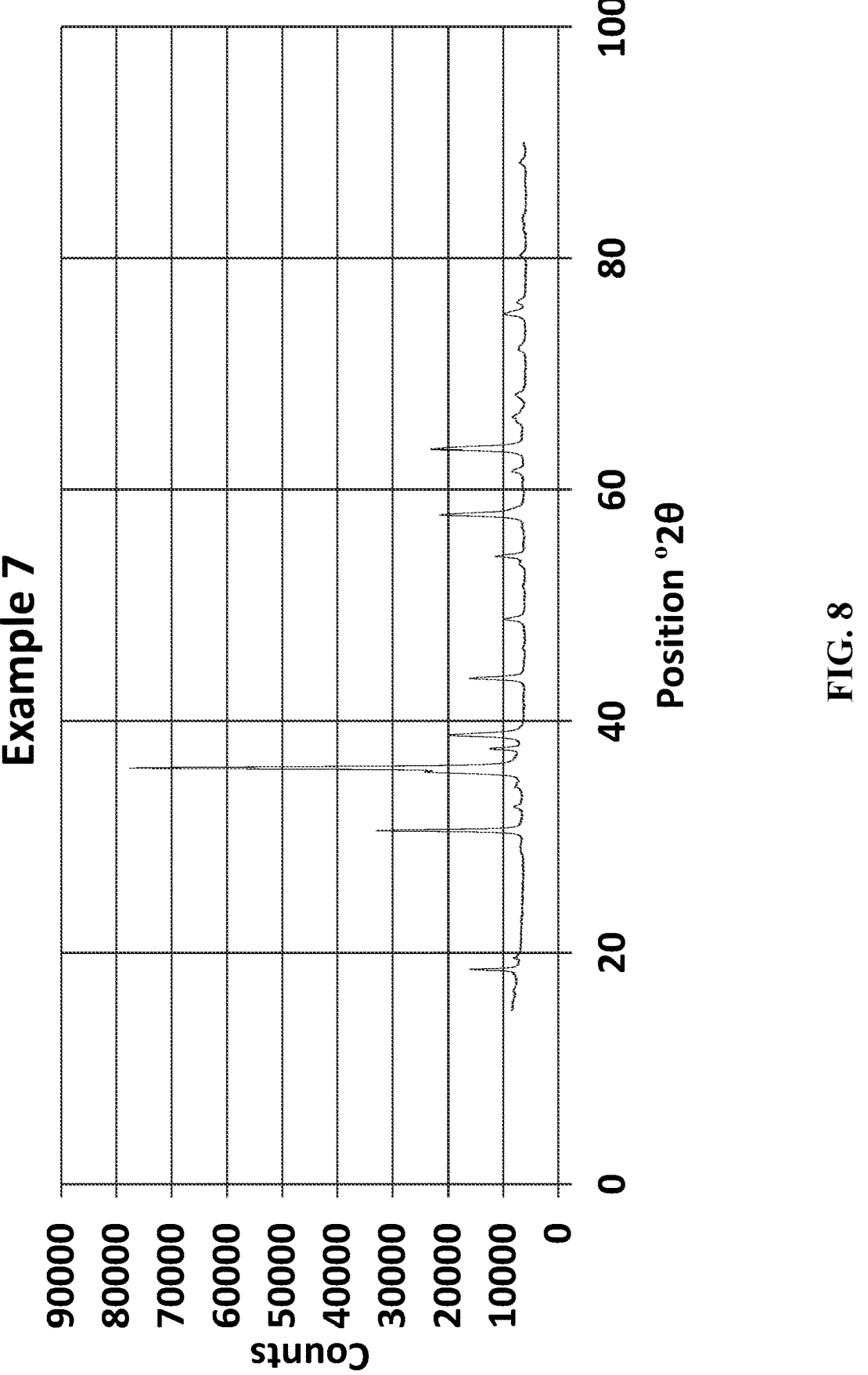
FIG. 8 is a graph showing the XRD spectra for the catalyst of Example 7, according to the examples.

FIG. 8 shows representative XRD peaks for CuO, $Cu_{1.5}Mn_{1.5}O_4$, and $Cu_3Mn_3O_8$ at 15.9, 17.0, 18.9, 20.0, 30.5, 32.6, 34.1, 35.5, 35.9, 36.0, 37.8, 43.9, 46.3 48.9, 51.7, 53.8, 54.2, 57.9, 61.7, 63.7, 63.9, 66.1, 68.1, 72.1, 72.3, 75.3, 76.0, 77.1, 80.0, 83.1, and 88.4 for the Example 7 catalyst.

Figure 9:
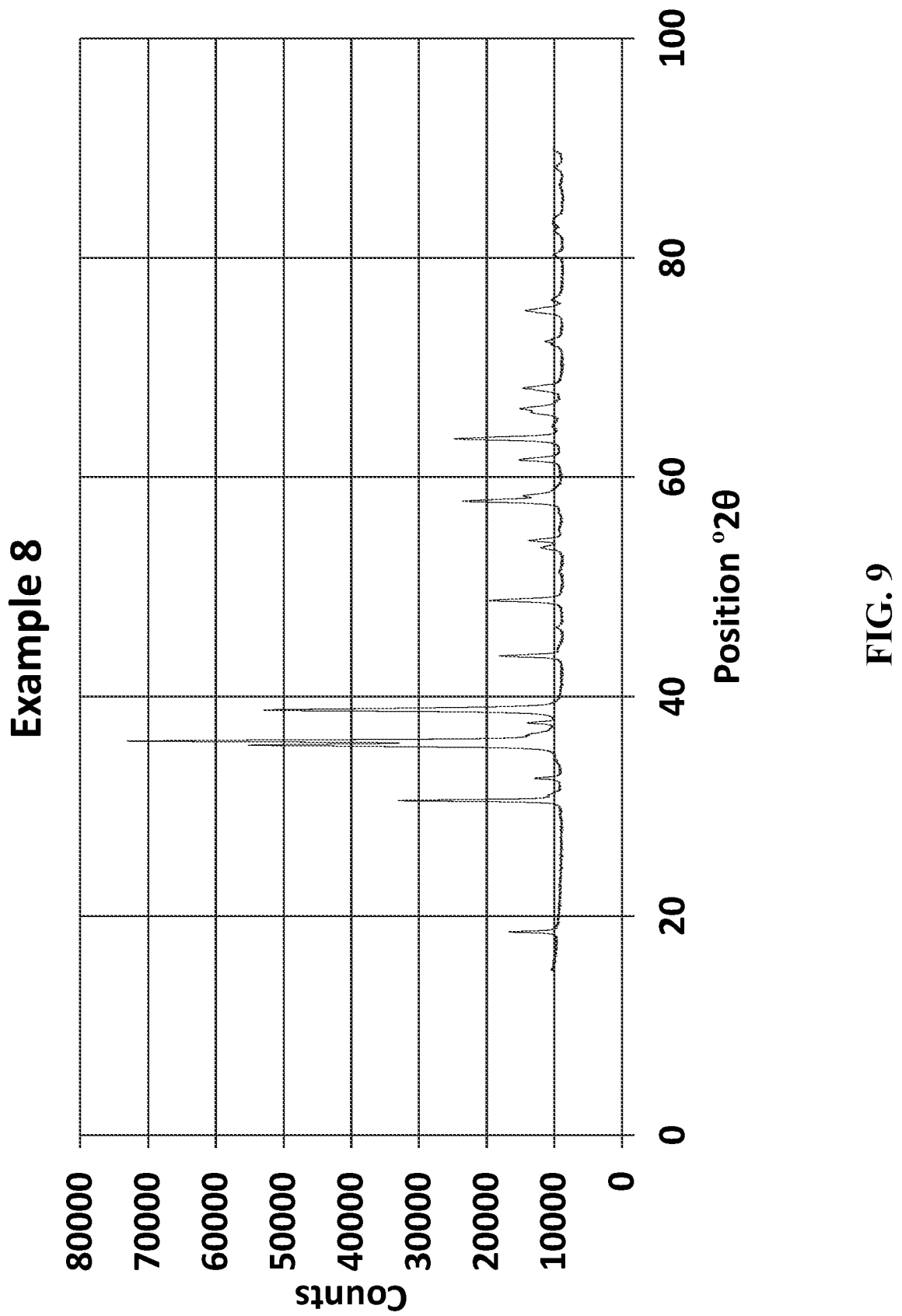
FIG. 9 is a graph showing the XRD spectra for the catalyst of Example 8, according to the examples.

FIG. 9 shows representative XRD peaks for CuO, $CuAl_2O_4$, and $Cu_{1.5}Mn_{1.5}O_4$ at 18.9, 30.5, 31.1, 32.6, 34.0, 35.5, 35.9, 36.7, 37.8, 38.9, 43.6, 44.6, 46.4 48.9, 51.2, 53.6, 54.2, 55.5, 57.9, 58.2, 59.3, 61.7, 63.5, 65.0, 65.9, 68.1, 72.2, 75.3, 76.1, 80.1, 82.1, 83.2, 83.6, 86.8, and 88.2 for the Example 8 catalyst.

As shown in Table 4 below, further analysis of Examples 2, 3, and 6 showed that there are about 60-66 wt % of CuO in spinel structures while there is about 34-39 wt % CuO in the form of tenorite structures:

TABLE 4

Crystallite Phases Compositions by XRD Analysis

| | Weight % of Crystal Phases in XRD Analysis | |
|---|---|---|
| | Spinel (summed) | Tenorite |
| Example 2 | 65.9 | 34.1 |
| Example 3 | 63.0 | 37.1 |
| Example 6 | 61.4 | 38.6 |

As shown in Table 5 below, crystallite size analysis showed that spinel structures have a crystallite size of about 12-15 nm and tenorite structures have a crystallite size of about 21-27 nm:

TABLE 5

Crystallite Size of Catalysts Analyzed by XRD

| | Crystallite Size by XRD Analysis, nm | |
|---|---|---|
| | Spinel | Tenorite |
| Example 2 | 12.5 | 21.8 |
| Example 3 | 12.9 | 26.8 |
| Example 6 | 14.5 | 22.2 |

U.S. Pat. No. 6,455,474 XRD shows CuO and $CuAl_2O_4$ crystal phases, this invention shows in addition to CuO, at least should have one of the following phases $CuAl_2O_4$, $Cu_{1.5}Mn_{1.5}O_4$, $Cu_3Mn_3O_8$, $Cu_{0.451}Mn_{0.594}O_2$, $Mn_2O_3$, and $MnAl_2O_4$—the last two not showing in these examples Example 9. One way to minimize catalyst metal leaching is to pre-reduce the catalyst. The catalyst of Example 5 was pre-reduced with hydrogen under pressurized conditions. The reduction procedure was as follows: 1. Reduce the catalyst at 250° C. and 2500 psig $H_2$ pressure for 4 hours in the solvent-75% dodecanol and 25% tetradecanol with 2000 RPM agitation in an autoclave. 2. After 4 hours reduction, cool down the autoclave to room temperature. Drain out the solvent (75% dodecanol and 25% tetradecanol) in the sample line (through frit) until some gas bubbles come out and the catalyst stays inside the reactor. 3. Depressurize the system to 250 psi. Charge the liquid feed (methyl ester; 396 g) liquid feed pump so that the effective catalyst loading is 0.8 wt %. 4. Run the reaction at 2500 psig $H_2$, 280° C., and 2000 rpm for 5 hours, taking 5 ml liquid sample every hour for product analysis to evaluate the catalyst performance. This catalyst also shows good alcohol yield with good activity.

Example 10. Catalytic performance. Catalytic activity and selectivity of the catalysts were evaluated by slurry phase hydrogenolysis/hydrogenation of a methyl ester (ME) and wax ester (WE) to a fatty alcohol. Catalyst performance evaluations were performed for both methyl ester hydrogenolysis/hydrogenation and wax ester hydrogenolysis/hydrogenation in one-liter autoclave (shown below). Table 6 provides the feedstock compositions.

TABLE 6

Feedstock compositions in fatty acid methyl ester feed.

| Compound | Amount (wt %) |
|---|---|
| C-8 ME | 0.00 |
| C-10 ME | 0.02 |
| C-12 ME | 74.83 |
| C-14 ME | 23.05 |
| C-16 ME | 0.57 |
| C-18:0 ME | 0.00 |
| C-18:1 ME | 0.00 |
| C-18:2 ME | 0.00 |
| C24 WE | 0.57 |
| 12:14 + 14:12 WE | 0.61 |

ME: methyl ester;
WE: wax ester

Procedure for ME hydrogenolysis/hydrogenation. The catalyst (0.8 wt %) is loaded into the autoclave with 452 g of a $C_{12}$-$C_{14}$ fatty acid methyl ester. The system is purged with $N_2$. Under agitation (2000 rpm), the temperature is ramped at 3° C./min to 280° C., at which point the autoclave is pressurized with hydrogen to 2500 psi. This point, is assigned time zero, to. Every hour, for 5 hours thereafter, a 5 ml liquid sample is collected and analyzed by gas chromatography. The total fatty alcohol yield was calculated summing the fatty alcohol concentration in gas chromatography analysis.

Procedure for WE hydrogenolysis/hydrogenation. The catalyst (0.75 wt %) is loaded into the autoclave with 454 g of a $C_{12}$-$C_{14}$ fatty alcohol. The system is purged with $N_2$. Under agitation (1500 rpm), the temperature is ramped at 3° C./min to 300° C., at which point the autoclave is pressurized with hydrogen to 4350 psi. A $C_{16}$-$C_{18}$ fatty acid (55 g; 27% $C_{16}$ acid and 72% $C_{18}$ acid) is then injected into the system. This point, is assigned time zero, to. At 1 hour, a 5 mL sample is collected, and a $C_{16}$-$C_{18}$ fatty acid (55 g) is then injected into the system. At the second and third hours, sampling and injection of fatty acid were conducted. The reaction was then run to 6 hours with sampling, but without further injection. Each sample (6 total) was then analyzed by gas chromatography. The total fatty alcohol yield was calculated summing the fatty alcohol concentration in gas chromatography analysis.

The saponification (SAP) value of each sample was calculated by wet titration. The conversion of fatty acid was calculated based on the % SAP value reduction. Conversion (%)=(SAP value in resulting feed mixture-SAP value in the product)*100/SAP value in resulting feed mixture.

Figure 10:
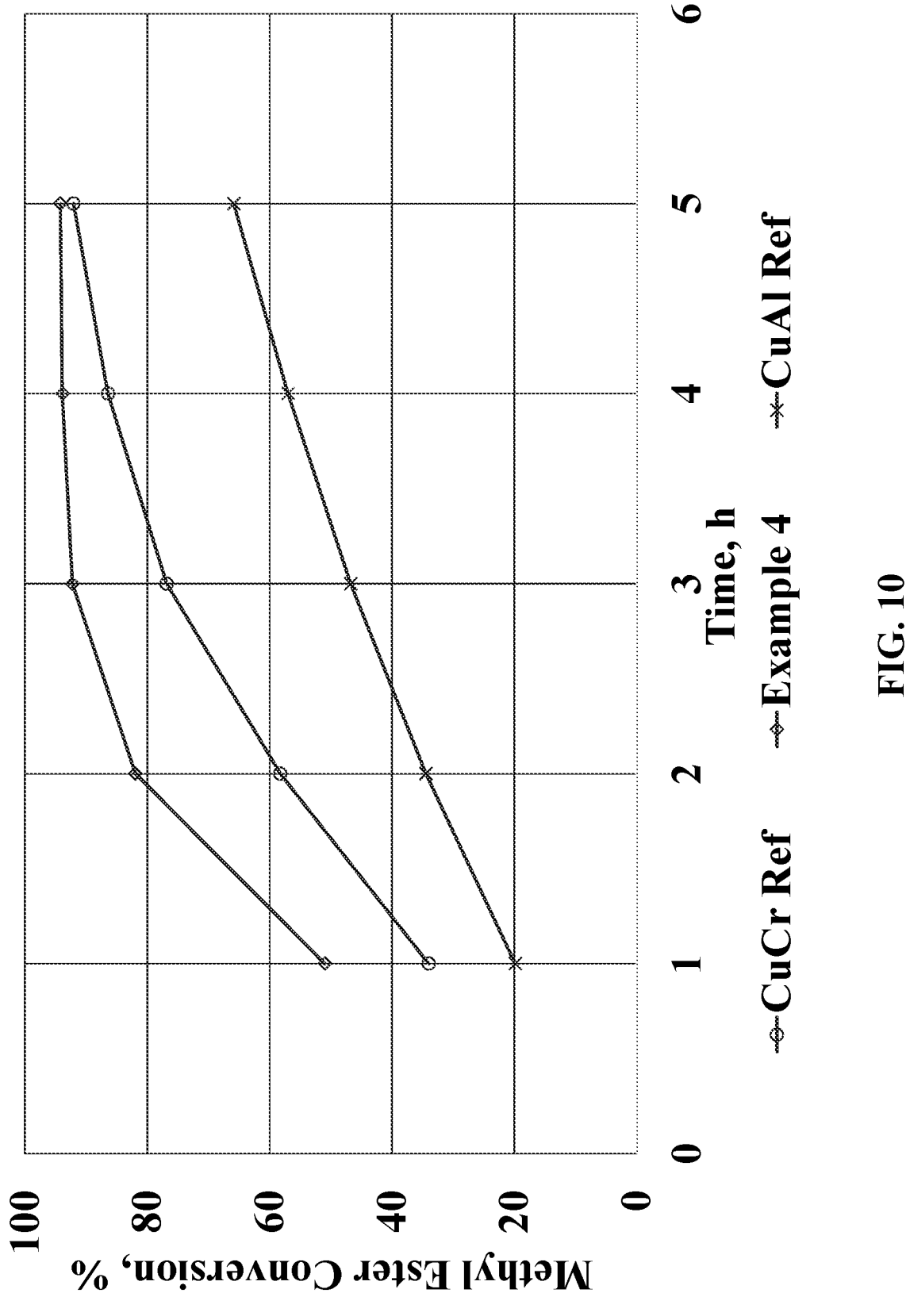
FIG. 10 is a graph comparing methyl ester conversion as a percentage as a function of time for a standard CuCr catalyst, a CuAl catalyst, and the described Cu—Mn—Al catalyst, according to the examples.
Figure 11:
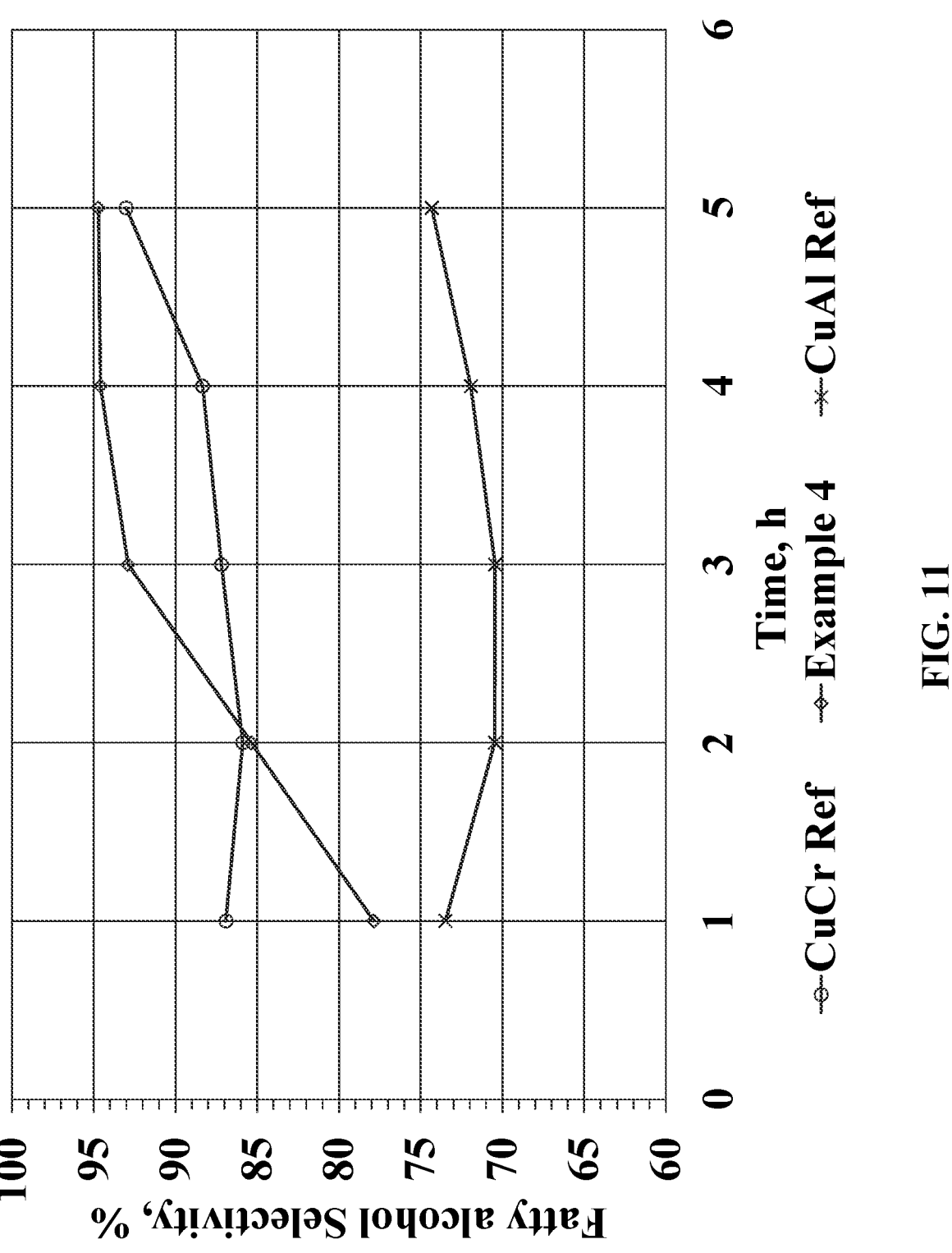
FIG. 11 is a graph comparing fatty alcohol selectivity as a percentage as a function of time for a standard CuCr catalyst, a CuAl catalyst, and the described Cu—Mn—Al catalyst, according to the examples.
Figure 12:
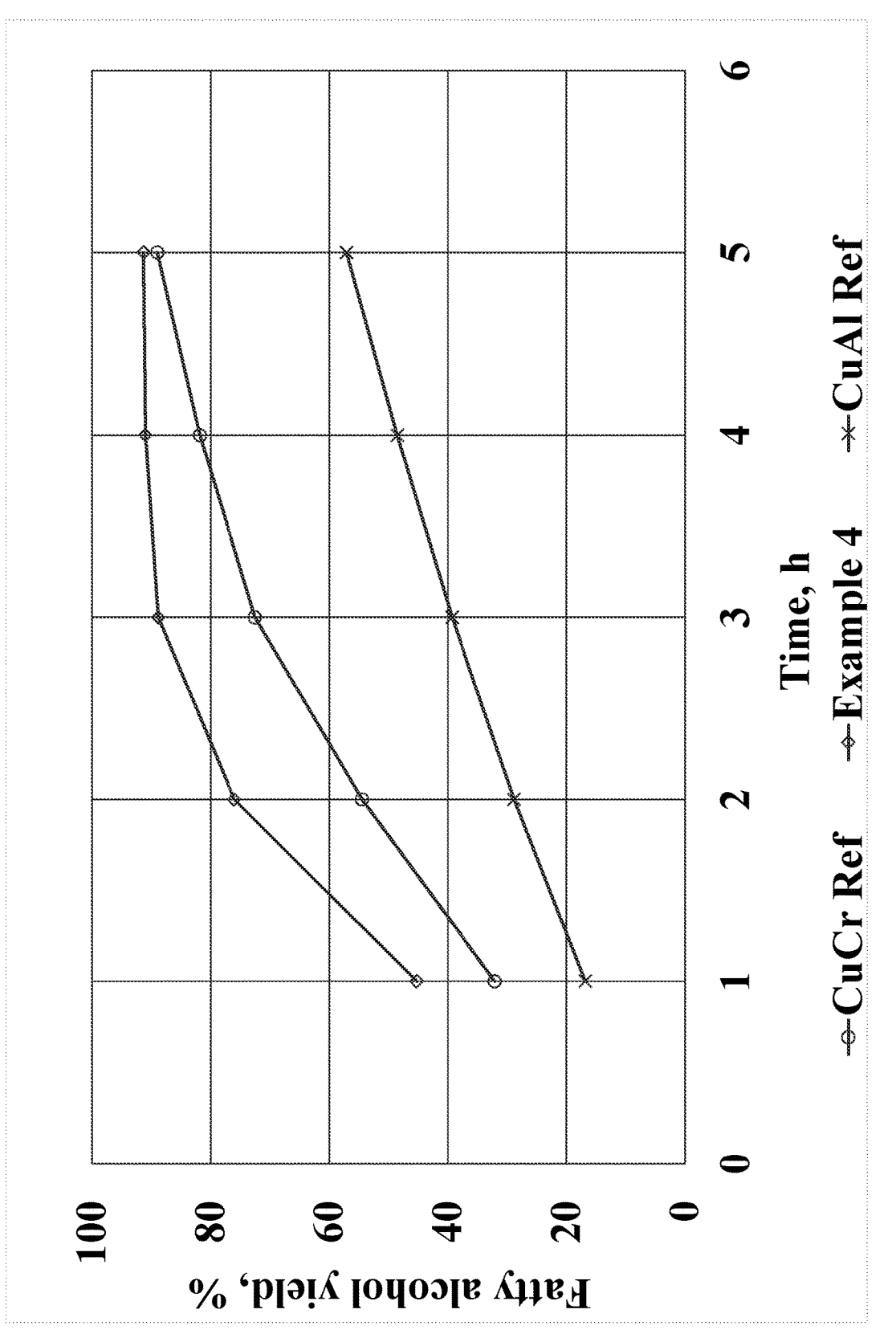
FIG. 12 is a graph comparing fatty alcohol yield as a percentage as a function of time for a standard CuCr catalyst, a CuAl catalyst, and the described Cu—Mn—Al catalyst, according to the examples.

Example 11. Comparison of catalyst performance of commercial CuCr and CuAl with current invented catalysts. Under the described testing conditions, for methyl ester hydrogenolysis/hydrogenation, CuAl powder catalyst (Comparative Example) underperforms the commercially used standard CuCr reference powder catalyst. With addition of Mn to CuAl as a promoter according to Example 4, the catalytic performance is significantly improved. FIGS. 10-12 illustrate the improvements. In FIGS. 10-12, as the reaction time progresses, the desired product fatty alcohol for CuMnAl catalyst Example 4 is always higher than that for the standard CuCr reference catalyst throughout the test time period. These results demonstrate that the CuMnAl powder catalyst is superior in performance to the CuCr powder catalyst for fatty methyl ester hydrogenolysis/hydrogenation applications.

Figure 13:
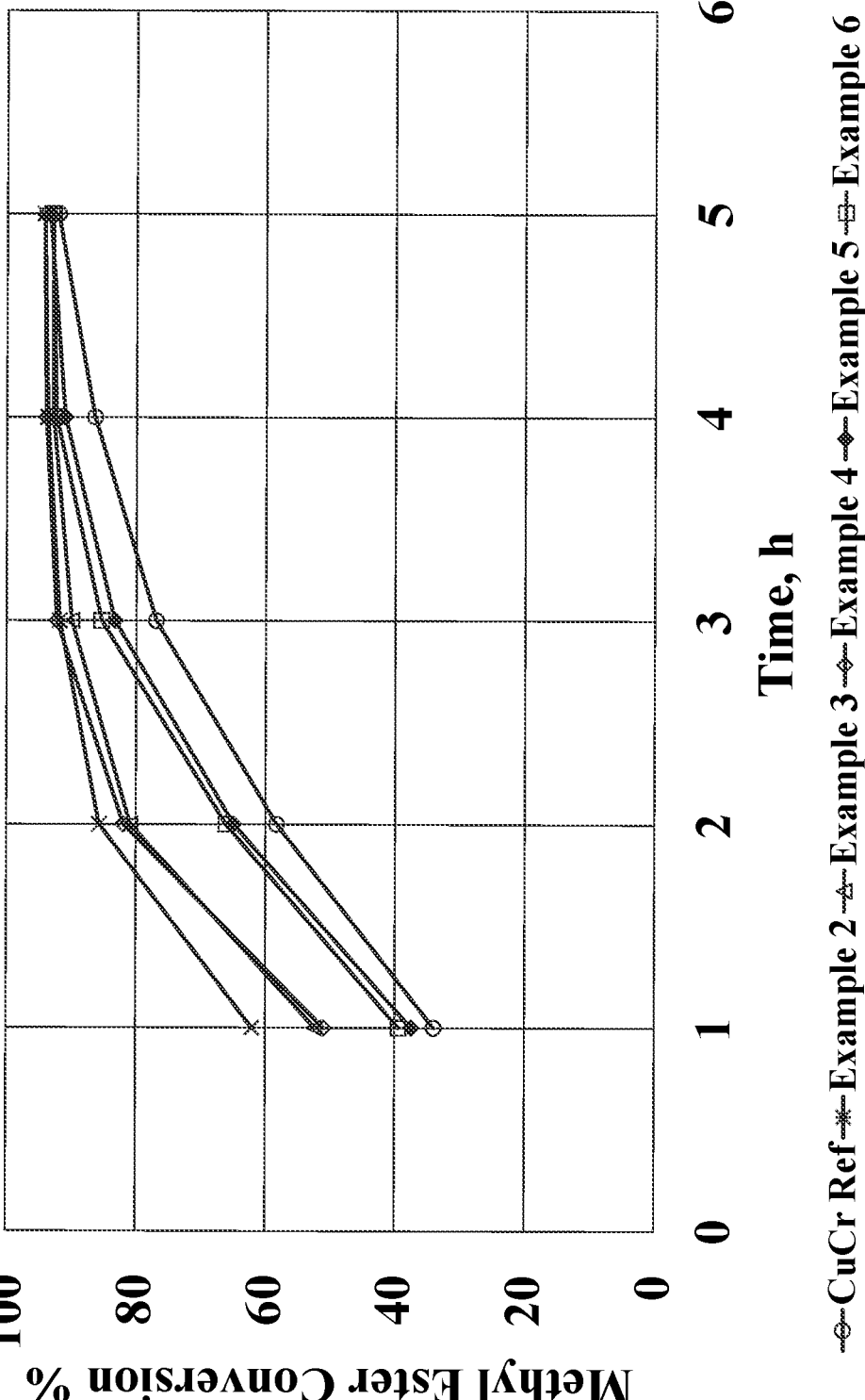
FIG. 13 is a graph comparing methyl ester conversion as a percentage as a function of time, according to the examples.
Figure 14:
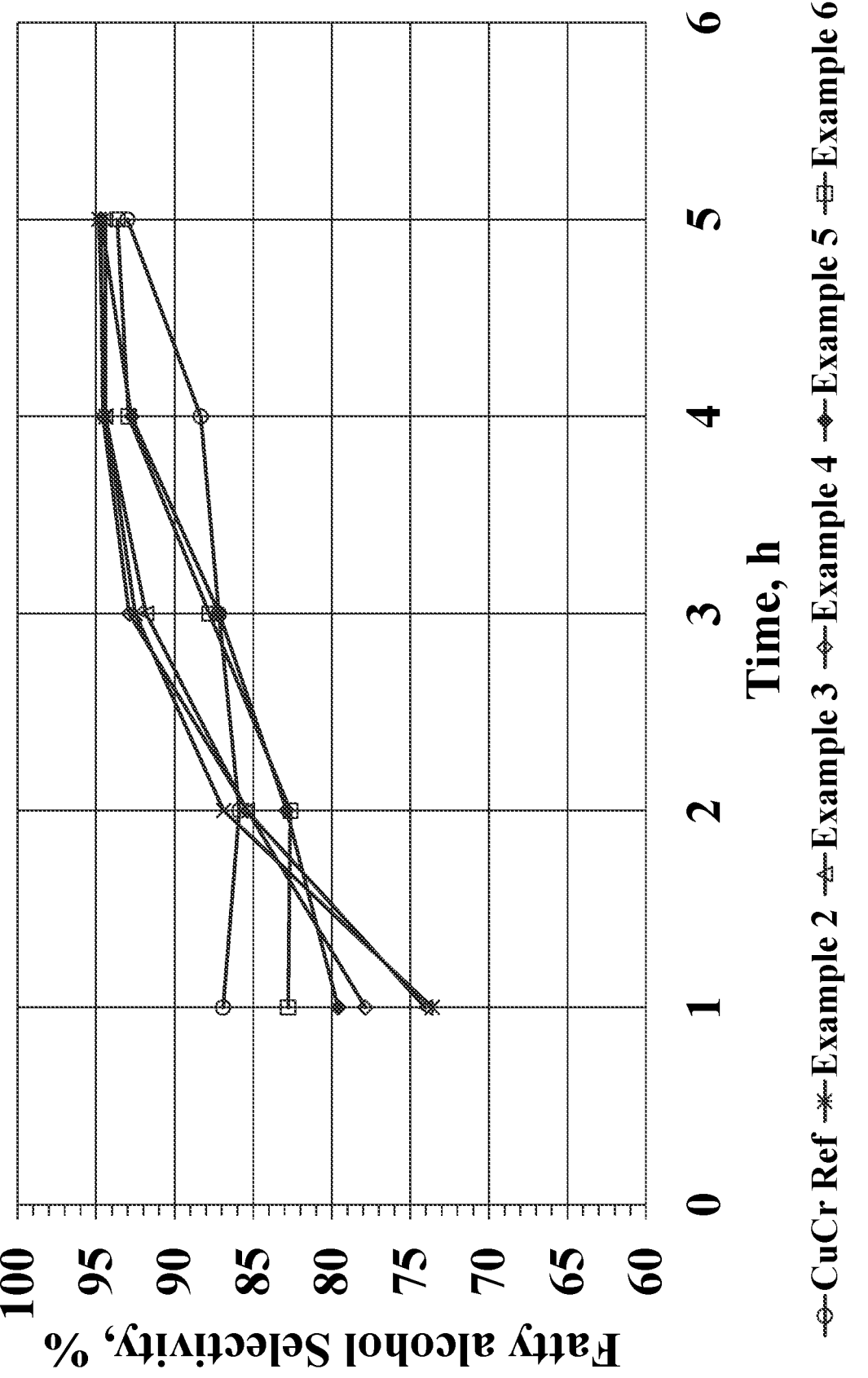
FIG. 14 is a graph comparing fatty alcohol selectivity as a percentage as a function of time, according to the examples.
Figure 15:
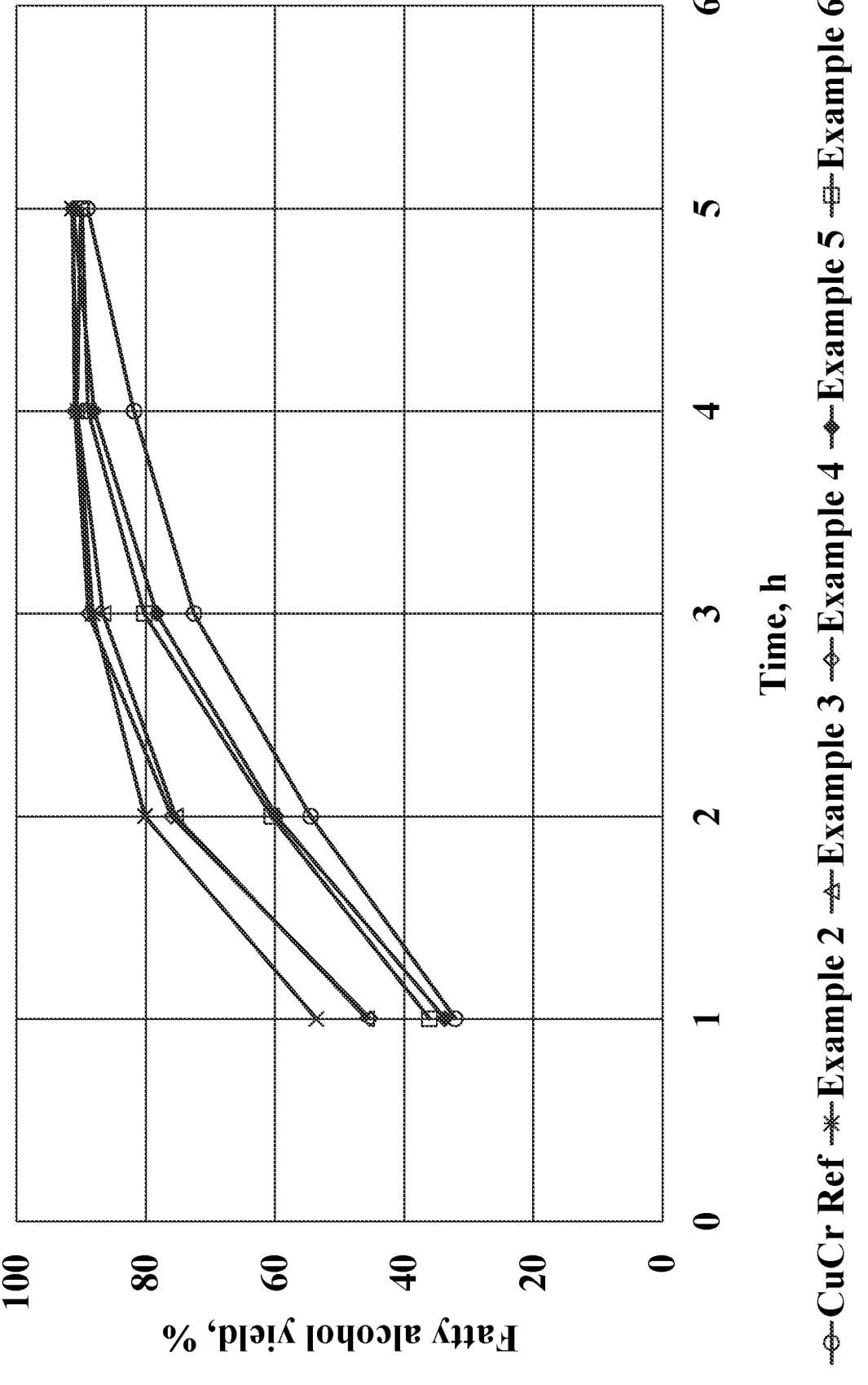
FIG. 15 is a graph comparing fatty alcohol yield as a percentage as a function of time, according to the examples.

Impact of BET surface area on catalytic performance. Lower calcination temperatures result in higher BET surface area, and therefore higher hydrogenolysis/hydrogenation activity. However, a high BET surface area powder catalyst is more susceptible to chemical attack, especially in the presence of acid components in the feedstock. This leads to undesirable leaching of the metals into the hydrogenolysis/hydrogenation product. When this material is calcined at a high enough temperature a spinel structure will be formed that is stable under the reaction conditions, i.e. for feedstocks that contain acid. The catalyst powder was calcined at different temperatures in Examples from 2 to 6 that produced the powders with different BET surface areas. These samples were tested for methyl ester hydrogenolysis/hydrogenation catalytic performance. The results are shown in FIGS. 13-15. The product alcohol yield curves show that low surface area (e.g. 20 and 40 m²/g) produce similar product yields throughout the test. Medium BET surface areas (e.g. 50 and 60 m²/g) have similar product yields as well. The results illustrate that CuMnAl powder with a BET surface area from 20 to 70 m²/g will exhibit better catalytic performance than commercially available standard CuCr reference powder catalyst, for fatty alcohol production.

Figure 16:
FIG. 16 is a graph comparing methyl ester conversion as a percentage as a function of time and comparing example 7 to a standard CuCr catalyst, according to the examples.
Figure 17:
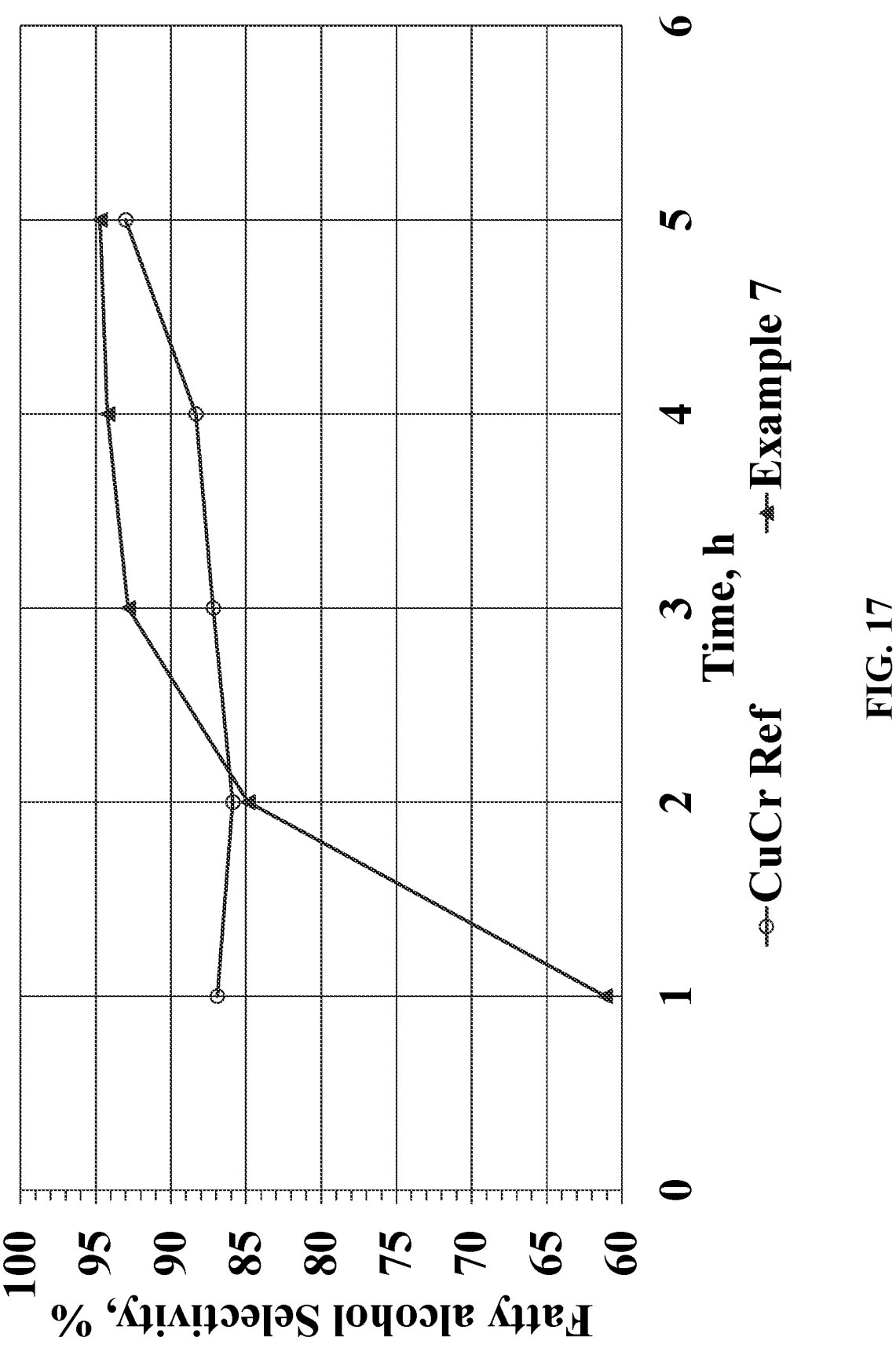
FIG. 17 is a graph comparing fatty alcohol selectivity as a percentage as a function of time and comparing example 7 to a standard CuCr catalyst, according to the examples.
Figure 18:
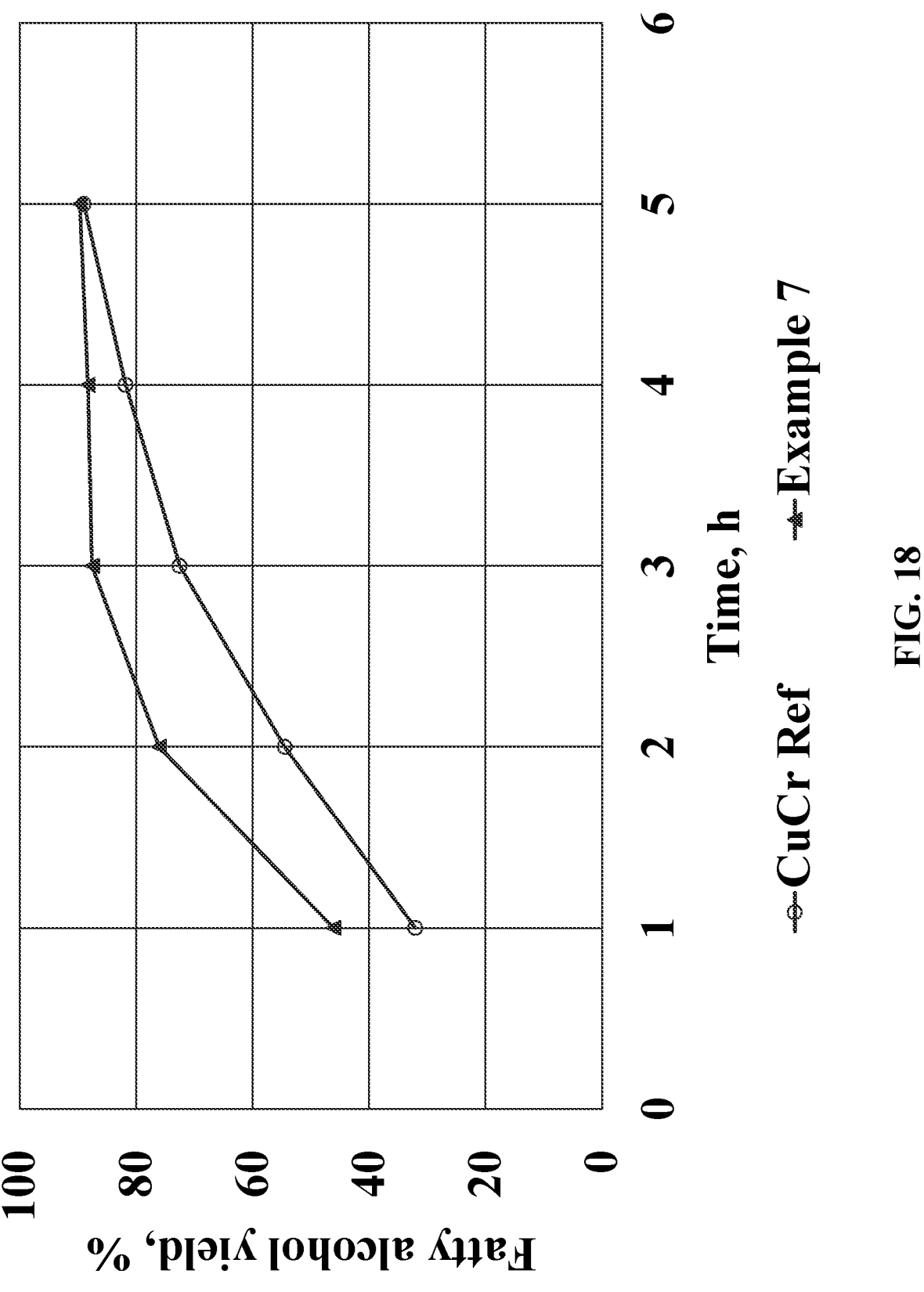
FIG. 18 is a graph comparing fatty alcohol yield as a percentage as a function of time and comparing example 7 to a standard CuCr catalyst, according to the examples.

Comparison of alcohol yield from Example 7 catalyst with CuCr catalyst. FIGS. 16-18 illustrate the methyl ester conversion percent versus hours for the CuCr reference catalysts in comparison to that for Example 7. Example 7 shows superior results.

Figure 19:
FIG. 19 is a graph comparing methyl ester conversion as a percentage as a function of time and comparing example 8 to a standard CuCr catalyst, according to the examples.
Figure 20:
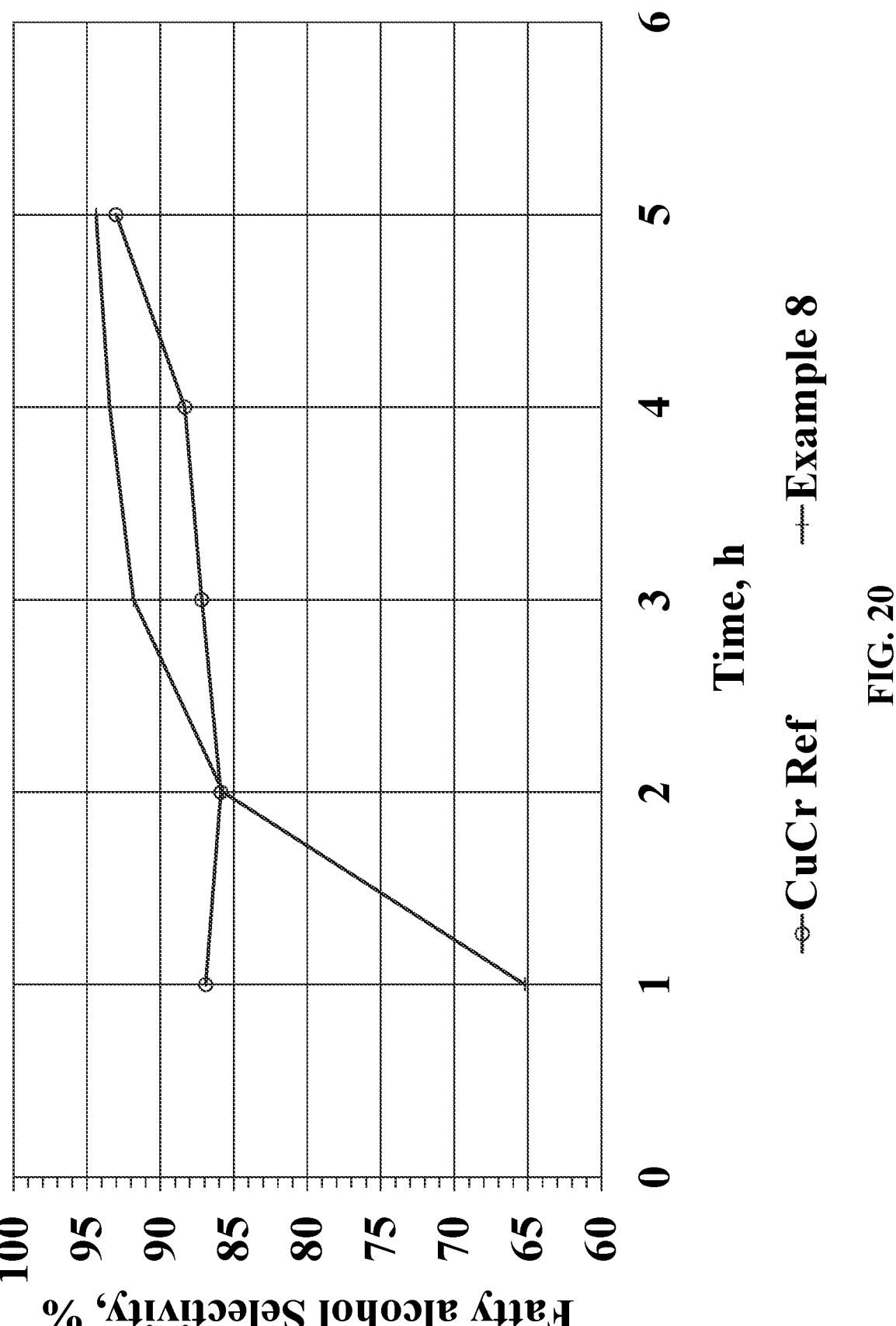
FIG. 20 is a graph comparing fatty alcohol selectivity as a percentage as a function of time and comparing example 8 to a standard CuCr catalyst, according to the examples.
Figure 21:
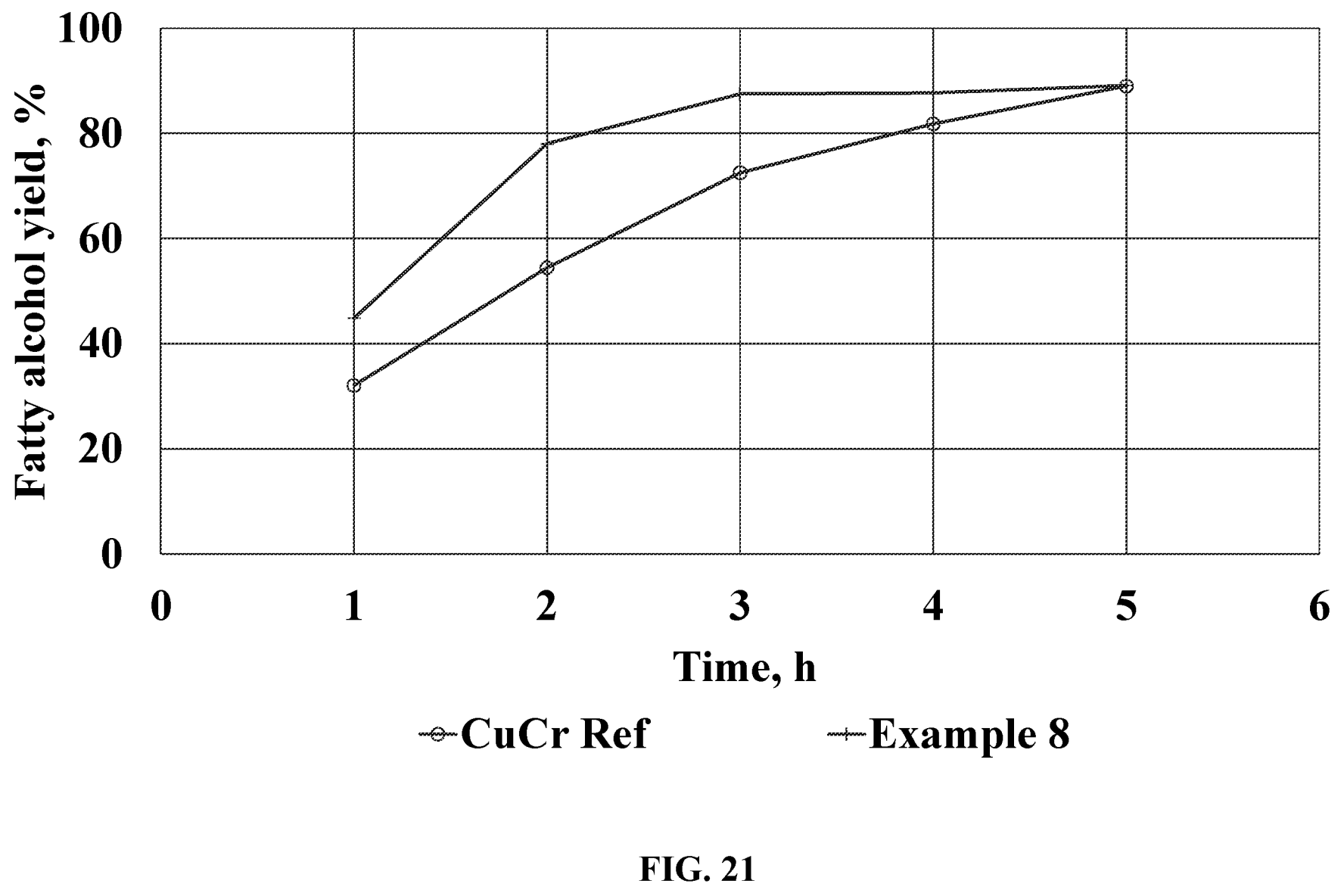

Comparison of alcohol yield from Example 8 catalyst with CuCr catalyst. FIGS. 19-21 illustrate the methyl ester conversion percent versus hours for the CuCr reference catalysts in comparison to that for Example 8. Example 8 shows superior results.

Figure 23:
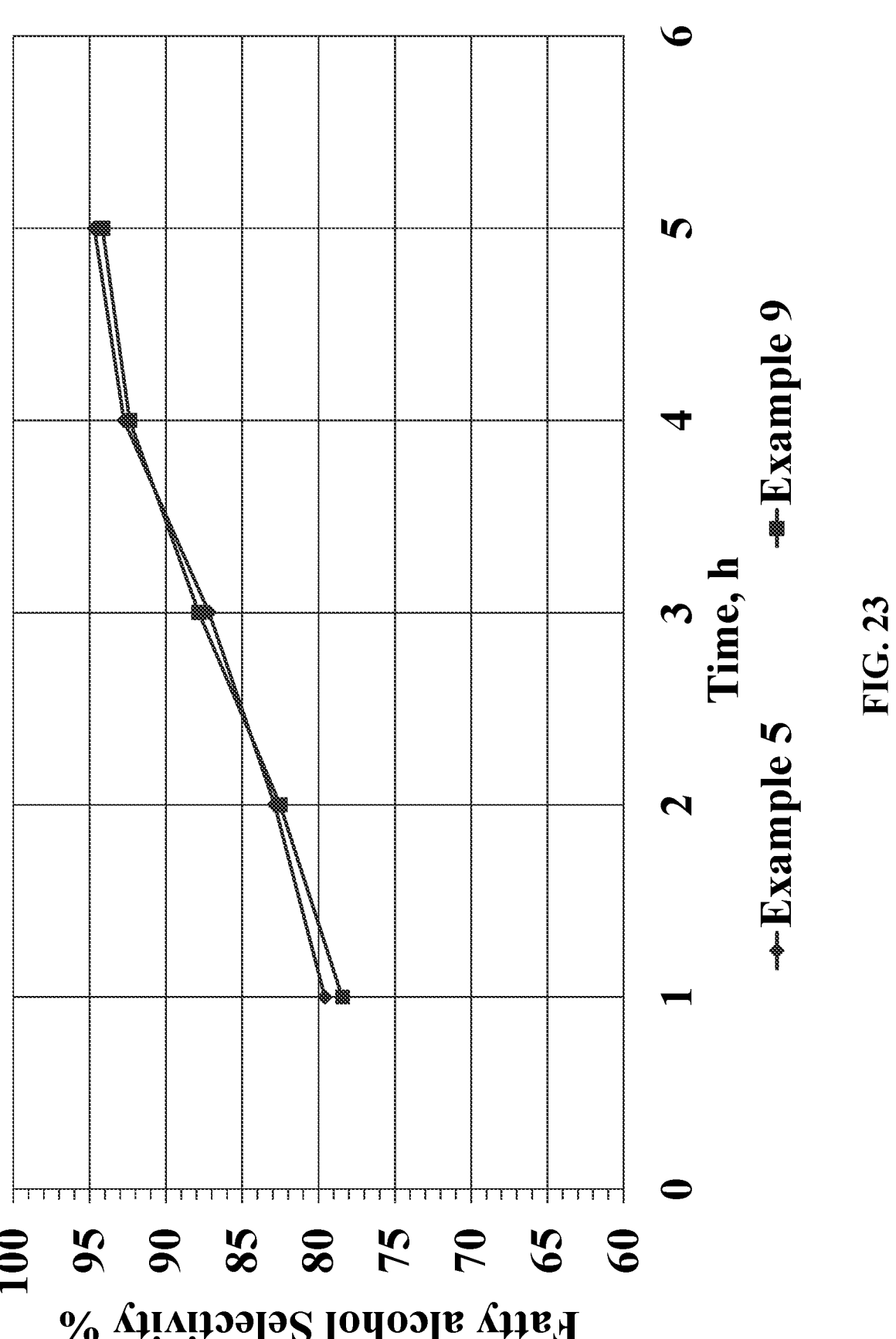
FIG. 23 is a graph comparing fatty alcohol selectivity as a percentage as a function of time and comparing examples 5 and 9, according to the examples.
Figure 24:
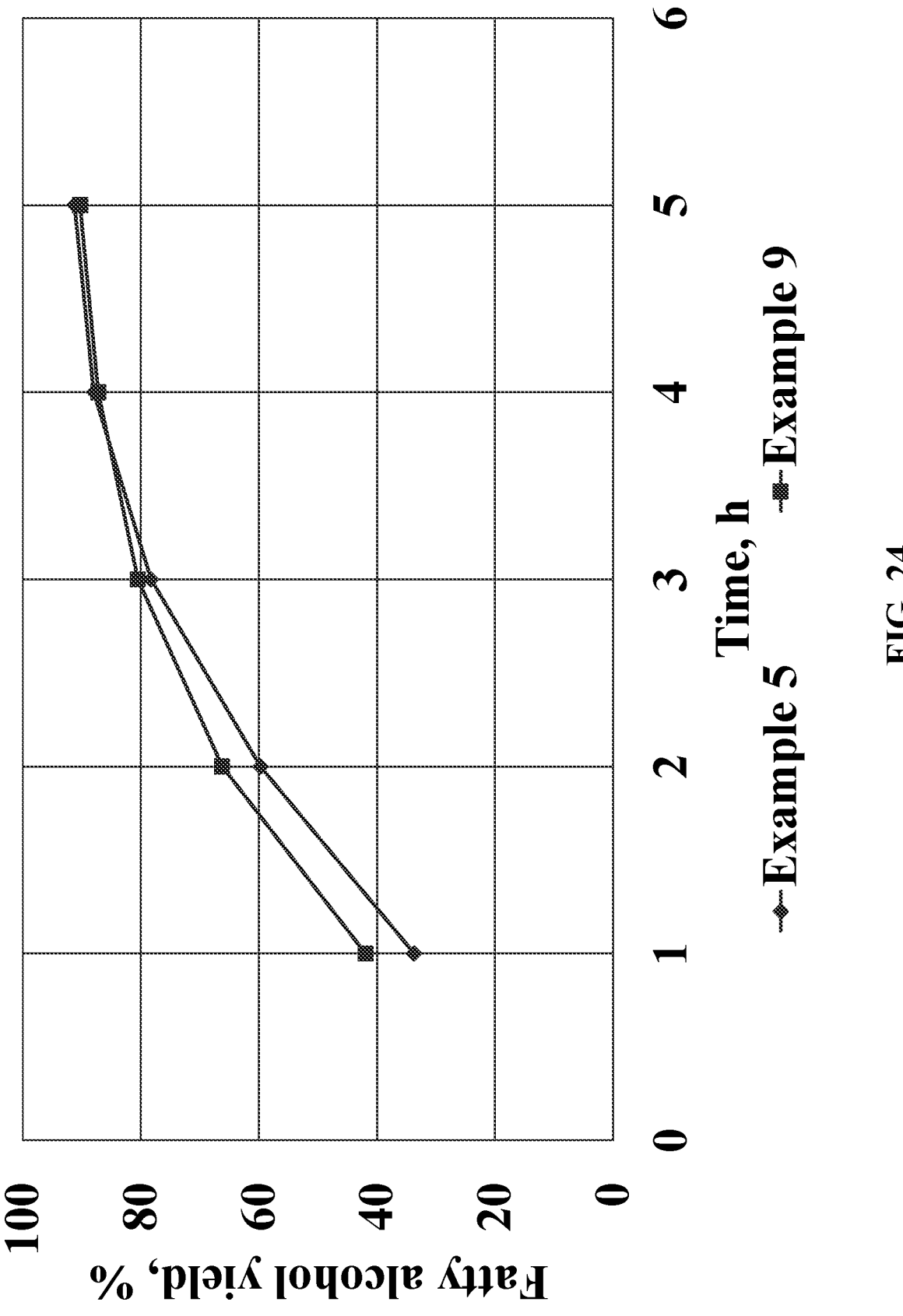
FIG. 24 is a graph comparing fatty alcohol yield as a percentage as a function of time and comparing examples 5 and 9, according to the examples.

Pre-reduced catalyst performance (Example 9). The pre-reduced catalyst evaluation results are comparable to the un-reduced catalyst. The results are shown in FIGS. 22-24.

Figure 25:
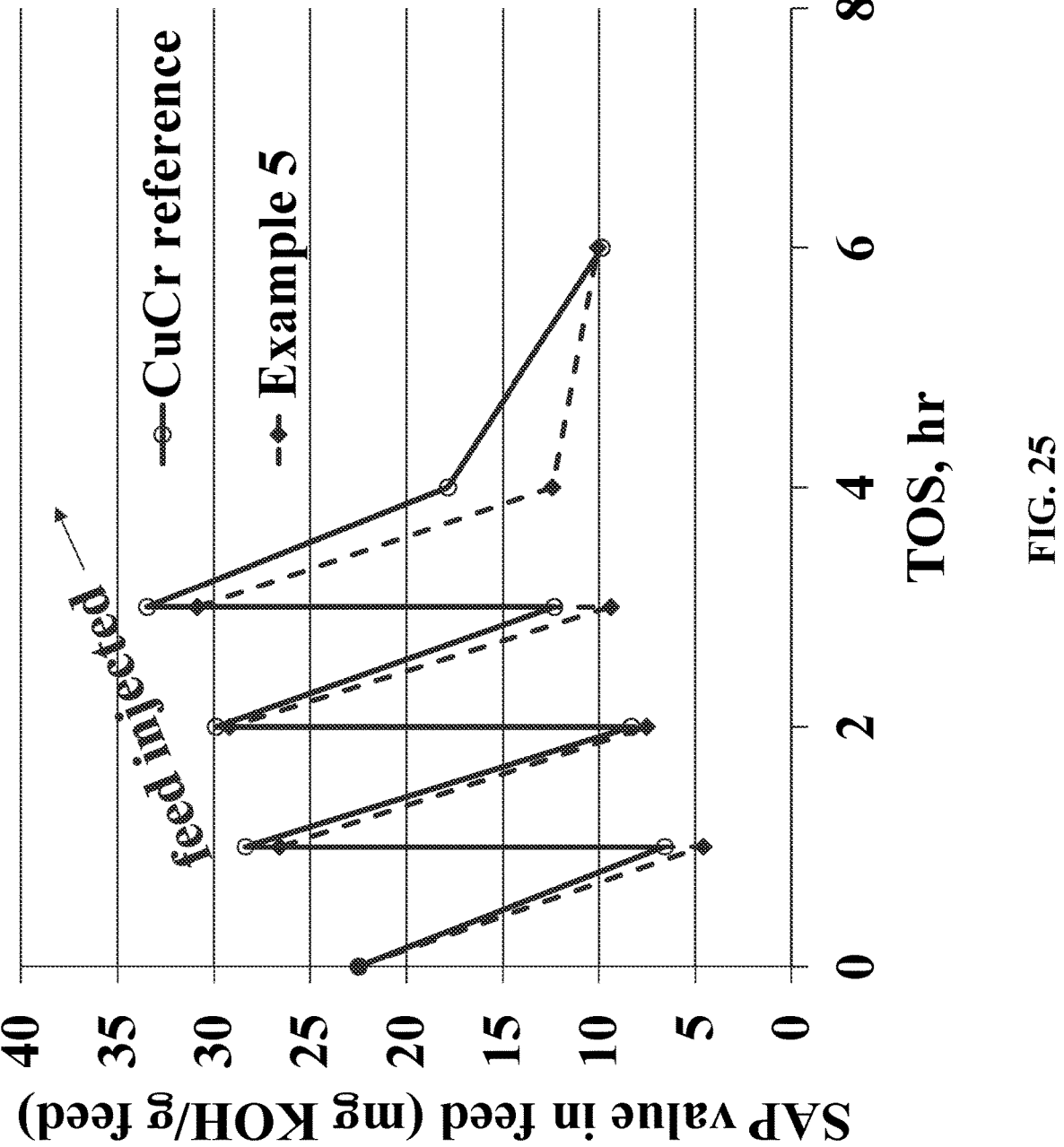
FIG. 25 is a graph of SAP value in the feed (mg KOH/h feed) as a function of time on stream ("TOS," hours), for a CuCr catalyst and Example 5, according to the examples.
Figure 26:
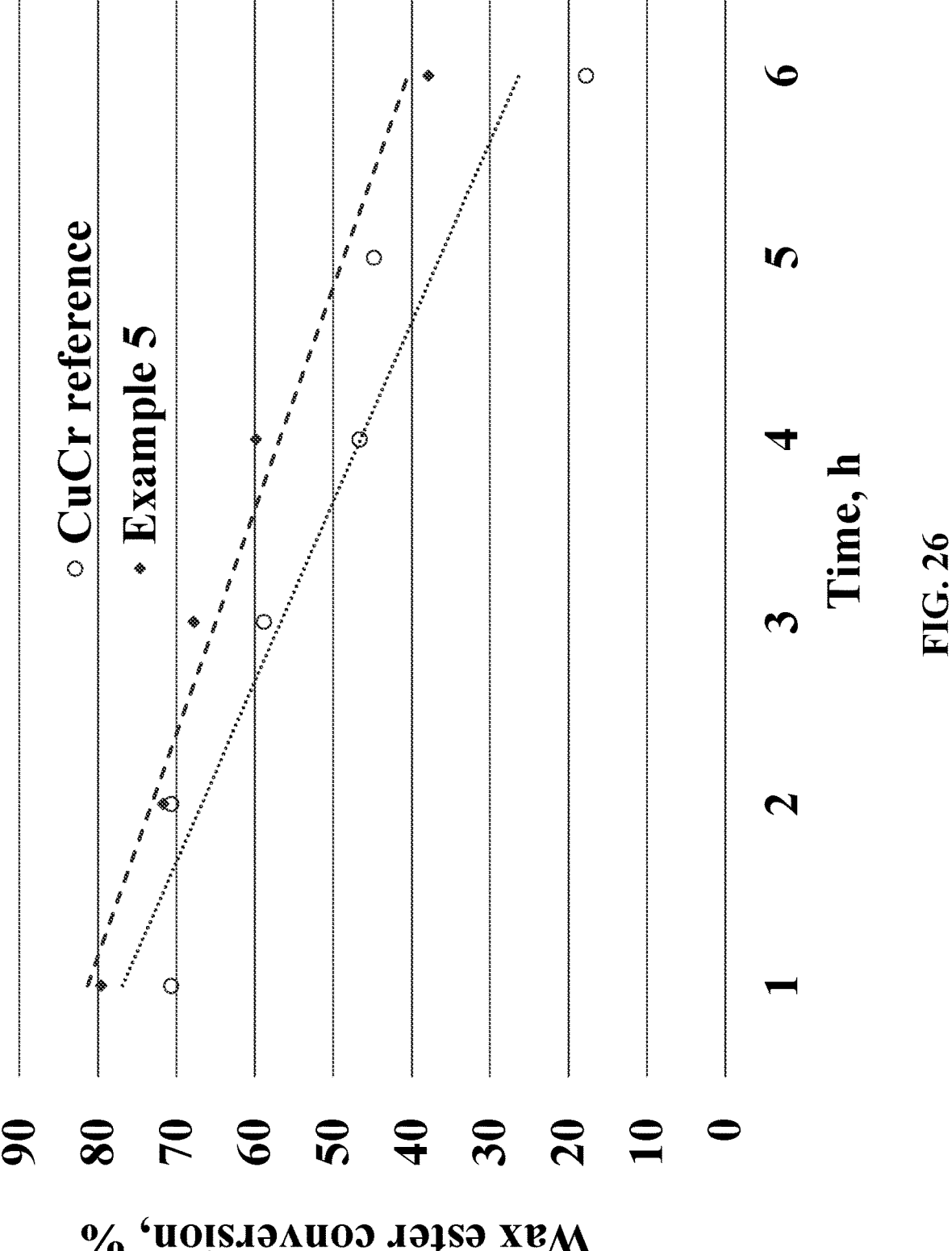
FIG. 26 is a graph of wax ester conversion as a percentage as a function of time for CuCr catalyst and Example 5, according to the examples.

Wax ester hydrogenolysis/hydrogenation performance comparison. The wax ester hydrogenolysis/hydrogenation performance comparison of the catalysts described above in comparison to the commercial CuCr catalyst is shown in FIGS. 25 and 26. In the series of experiments, a hydrogenolysis/hydrogenation product was withdrawn every hour for analysis, then inject new fatty acid as feed in the first four hours. The FIGs. shows that after 4th injection, as the reaction time continues, the residual wax ester reduces, so does the ester conversion as it approaches to equilibrium. Catalyst Example 5 shows consistently higher wax ester conversion than the standard CuCr reference catalyst throughout the testing period. Table 7 shows a comparison of final SAP value of the liquid production at about 6 h and conversion for the standard CuCr reference catalyst and Example 5 catalyst in slurry phase wax ester hydrogenolysis provides the final SAP value of the liquid product after reaction for 6 h. In particular, the saponification (SAP) value is expressed as mg KOH consumed per g of feed and measures the amount of fatty acid wax ester and fatty acids present in the feed. The catalyst of Example 5 converts more fatty acid wax ester to fatty alcohol compared to the commercially available standard CuCr reference catalyst. Consequently, the catalyst of Example 5 has a lower final SAP value in the liquid products at a reaction time of about 6 h. Thus, Example 5 exhibited higher conversion than the standard CuCr reference catalyst.

TABLE 7

| Comparison of final SAP value in the liquid product after 6 h reaction for two catalysts. | | |
|---|---|---|
| SAP value of total accumulated Feed 67.9. | Final SAP Value at 6 h | Overall Conversion, % |
| Commercial CuCr | 8.1 | 88 |
| Example 5 | 6.2 | 91 |

Catalyst filtration properties. The spent catalyst separation experiments (both centrifuge separation and filtration) were conducted to compare the catalyst filterability. The results show that CuMnAl catalysts have comparable separation properties to the standard CuCr reference catalyst.

Procedure for centrifugation. The spent catalyst slurry with the liquid products and unreacted fatty acid methyl ester are centrifuged at about 10,000 rpm (revolutions per minute) for about 3 minutes (min). The top 35 mL of liquid was collected and observed to identify floating particles. The separation efficiency is measured qualitatively based on the color and fine particles floating in the collected liquid. Centrifuge separation tests show that both current inventive catalyst and CuCr provide a clear liquid product. To confirm this, the liquid products were analyzed for metal leaching from catalysts. As shown in Table 8, the catalysts described herein have lower leaching of copper than the commercial CuCr catalyst.

TABLE 8

| Metal Leaching Test. | | | | | |
|---|---|---|---|---|---|
| Catalyst | Hours on stream | Al (ppm) | Cu (ppm) | Mn (ppm) | Cr (ppm) |
| CuCr Reference | 6 | — | 5 | <1 | <1 |
| Example 5 | 6 | 2 | <1 | <1 | — |

Procedure for filtration. Spent catalyst slurry (12 mL, well mixed) is pulled into a syringe. A syringe filter (0.45μ) is then seated on the tip of the syringe, and the filtrate is pressed through the filter. The speed with which the material was filed was then timed. The filter was changed if no filtrate passed with maximum hand pressure. The timer was stopped when 12 mL of the slurry was filtered. This test qualitatively estimates the time required for making the same amount of filtrate using 0.45 m filter. The results are presented in Table 9.

TABLE 9

| Filter/time Results. | |
|---|---|
| Catalyst | Time to Collect 12 ml liquid product, min |
| CuCr | 35 |
| Example 4 | 80 |

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims.

What is claimed is:

1. A powder form hydrogenolysis/hydrogenation catalyst comprising:
   copper oxide;
   manganese oxide; and
   alumina;
   wherein the hydrogenolysis/hydrogenation catalyst has a Brunauer-Emmett-Teller ("BET") surface area of about 5 to about 75 $m^2/g$,
   wherein the catalyst, when calcined, exhibits particle size distribution $d_{50}$ from about 4 μm to about 12 μm in diameter,
   wherein the catalyst, when calcined, exhibits spinel structure at about 55 to about 70 percent by weight of the CuO in the catalyst and exhibits tenorite structure at about 30 to about 45 percent by weight of the CuO in the catalyst, and
   wherein the hydrogenolysis/hydrogenation catalyst is substantially free of chromium and is not in the presence of a binder.

2. The hydrogenolysis/hydrogenation catalyst of claim 1, wherein the hydrogenolysis/hydrogenation catalyst exhibits a crystal phase of $CuAl_2O_4$, $Cu_{1.5}Mn_{1.5}O_4$, $Cu_3Mn_3O_8$, $Cu_{0.451}Mn_{0.594}O_2$, $Mn_2O_3$, $MnAl_2O_4$, or a combination of any two or more thereof, and wherein the BET surface area of the hydrogenolysis/hydrogenation catalyst is about 20 $m^2/g$ to about 70 $m^2/g$.

3. The hydrogenolysis/hydrogenation catalyst of claim 1, wherein the hydrogenolysis/hydrogenation catalyst comprise spinel structures having a crystallite size about 15 nm or less or wherein the hydrogenolysis/hydrogenation catalyst comprises tenorite structures having a crystallite size of about 20 nm to about 30 nm.

4. The hydrogenolysis/hydrogenation catalyst of claim 1 comprising CuO from about 35 wt % to about 65 wt %, $Mn_2O_3$ from about 8 wt % to about 60 wt %, and $Al_2O_3$ from about 2 wt % to about 40 wt %.

5. The hydrogenolysis/hydrogenation catalyst of claim 1 exhibiting a crystal phase of CuO and one or more phases selected from $CuAl_2O_4$, $Cu_{1.5}Mn_{1.5}O_4$, $Cu_3Mn_3O_8$, $Cu_{0.451}Mn_{0.594}O_2$, $Mn_2O_3$, $MnAl_2O_4$.

6. A method of hydrogenating a carbonyl-containing organic compound, the method comprising contacting the carbonyl-containing organic compound with the hydrogenolysis/hydrogenation catalyst of claim 1.

7. The method of claim 6, wherein the method is carried out in a slurry phase reactor.

8. A catalyst comprising:
   copper oxide;
   manganese oxide; and
   alumina;
   wherein the catalyst has a Brunauer-Emmett-Teller ("BET") surface area of about 5 to about 75 $m^2/g$,
   wherein the catalyst, when calcined, exhibits particle size distribution $d_{50}$ from about 4 μm to about 12 μm in diameter,
   wherein the catalyst, when calcined, exhibits spinel structure at about 55 to about 70 percent by weight of the CuO in the catalyst and exhibits tenorite structure at about 30 to about 45 percent by weight of the CuO in the catalyst, and
   wherein the catalyst is substantially free of chromium and is not in the presence of a binder.

* * * * *